US012708365B2

(12) United States Patent
Choi

(10) Patent No.: US 12,708,365 B2
(45) Date of Patent: Aug. 18, 2026

(54) CARTRIDGE FOR SURGICAL INSTRUMENT AND SURGICAL INSTRUMENT INCLUDING THE CARTRIDGE

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 19/177,162

(22) Filed: Apr. 11, 2025

(65) Prior Publication Data

US 2025/0318830 A1 Oct. 16, 2025

(30) Foreign Application Priority Data

Apr. 15, 2024 (KR) ........................ 10-2024-0050320

(51) Int. Cl.
*A61B 17/00* (2006.01)
*A61B 17/072* (2006.01)

(52) U.S. Cl.
CPC ................... *A61B 17/07207* (2013.01); *A61B 2017/00862* (2013.01); *A61B 2017/07271* (2013.01)

(58) Field of Classification Search
CPC .... A61B 17/07207; A61B 2017/00862; A61B 2017/07271; A61B 2017/07278; A61B 2017/07285; A61B 2090/034; A61B 2017/2946
USPC ....................................................... 227/176.1
See application file for complete search history.

(56) References Cited

U.S. PATENT DOCUMENTS

2014/0263570 A1* 9/2014 Hopkins .......... A61B 17/07207 227/176.1
2020/0085433 A1* 3/2020 Aranyi ............. A61B 17/07207

FOREIGN PATENT DOCUMENTS

| | | | | |
|---|---|---|---|---|
| CN | 115707431 | * | 2/2023 | ........... A61B 17/072 |
| CN | 115707431 | A | 2/2023 | |
| EP | 2959845 | A1 | 12/2015 | |
| EP | 3412222 | A1 | 12/2018 | |
| JP | 2020-501789 | A | 1/2020 | |
| KR | 10-2024-0035932 | A | 3/2024 | |

* cited by examiner

*Primary Examiner* — Jacob A Smith
(74) *Attorney, Agent, or Firm* — Bridgeway IP Law Group, PLLC; Sang Ho Lee; Hyun Woo Shin

(57) ABSTRACT

A surgical instrument includes an end tool rotatable in at least one direction, the end tool including a jaw unit having a first jaw configured to accommodate a cartridge, and a second jaw facing the first jaw, a working member configured to be movable in a lengthwise direction of the first jaw, and a first elastic member disposed on a proximal side of the first jaw and configured to restrict a movement of the working member depending on whether the cartridge is accommodated in the first jaw, wherein when the cartridge is disposed on the first jaw, one end of the first elastic member is supported by the cartridge and then elastically deformed, and the first elastic member releases the restriction on the movement of the working member.

12 Claims, 20 Drawing Sheets

10
200
400
100
111
112
Z
Y
X 101
107
151
144
142
180
143
141
110
112
111
102

CARTRIDGE FOR SURGICAL INSTRUMENT AND SURGICAL INSTRUMENT INCLUDING THE CARTRIDGE

CROSS-REFERENCE TO RELATED APPLICATION

This application is based on and claims priority under 35 U.S.C. § 119 to Korean Patent Application No. 10-2024-0050320, filed on Apr. 15, 2024, in the Korean Intellectual Property Office, the disclosure of which is incorporated by reference herein in its entirety.

BACKGROUND

1. Field

The present disclosure relates to a surgical instrument, and more particularly, to a surgical instrument that is mountable on a robotic arm or manually operable for use in laparoscopic surgery or various other surgical procedures.

2. Description of the Related Art

In recent years, laparoscopic surgery has been actively utilized to reduce postoperative recovery time and complications through small incisions. Laparoscopic surgery is a surgical method in which a plurality of small holes are drilled in the abdomen of a patient and the inside of the abdominal cavity is observed through these holes, and is widely used in general surgery and the like.

In performing laparoscopic surgery, a suturing instrument inserted into the body is used to suture a surgical site in the abdominal cavity, and a surgical stapler for suturing the surgical site by using medical staples is used as the suturing instrument.

In general, surgical staplers are medical instruments frequently used for cutting and anastomosis of organs in abdominal and thoracic surgery. Surgical staplers include open staplers used in thoracotomy or laparotomy, and endo staplers used in thoracoscopy and laparoscopy.

Surgical staplers enable anastomosis of organs simultaneously with cutting of a surgical site, and thus have the advantage of shortening the operation time and achieving accurate suturing of the surgical site. In addition, surgical staplers have been widely used in modern surgical operations because they have the advantage of faster recovery and less scarring than when using surgical sutures for tissue cutting and suturing. In particular, surgical staplers have been widely used in cancer surgery to cut cancer tissue and suture a cut site.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

SUMMARY

The present disclosure relates to a surgical instrument, for use in laparoscopic surgery or various other surgical procedures, that is mountable on a robotic arm or manually operable, and has a structure that prevents a working member from moving forward when no staples are arranged in the surgical instrument.

Additional aspects will be set forth in part in the description which follows and, in part, will be apparent from the description, or may be learned by practice of the presented embodiments of the disclosure.

In an embodiment of the present disclosure, a surgical instrument may include an end tool rotatable in at least one direction, the end tool which may include a jaw unit including a first jaw configured to accommodate a cartridge, and a second jaw facing the first jaw, a working member configured to be movable in a lengthwise direction of the first jaw, and a first elastic member disposed on a proximal side of the first jaw and configured to restrict a movement of the working member depending on whether the cartridge is accommodated in the first jaw, and when the cartridge is disposed in the first jaw, one end of the first elastic member is supported by the cartridge and then elastically deformed, and the first elastic member releases a restriction on the movement of the working member.

In another embodiment of the present disclosure, the working member may include a locking protrusion protruding from one side of a main body and configured to restrict the movement of the working member when the cartridge is not disposed in the first jaw.

In the other embodiment of the present disclosure, the working member may have a first slit defined by cutting a portion of the main body, and the locking protrusion may protrude from the main body toward the first slit.

In the other embodiment of the present disclosure, the first elastic member may include a locking flange disposed in the first slit and configured to restrict the movement of the working member by engaging with the locking protrusion when the cartridge is not disposed in the first jaw.

In the other embodiment of the present disclosure, when the cartridge is disposed in the first jaw, a position of the locking flange may be changed by elastic deformation of the first elastic member, and the restriction on the movement of the working member caused by an engagement between the locking flange and the locking protrusion is released, and the working member may be movable forward toward a distal side of the first jaw.

In the other embodiment of the present disclosure, the first elastic member may include a locking groove corresponding to the locking protrusion, and configured to restrict the movement of the working member by engaging with the locking protrusion when the cartridge is not disposed in the first jaw.

In the other embodiment of the present disclosure, the locking groove may be concavely defined at one side of a seating portion of the first elastic member, the seating portion being seated on the first jaw.

In the other embodiment of the present disclosure, when the cartridge is disposed in the first jaw, a position of the locking groove may be changed by elastic deformation of the first elastic member, and the restriction on the movement of the working member caused by an engagement between a locking flange and the locking protrusion is released, and the working member may be movable forward toward a distal side of the first jaw.

In the other embodiment of the present disclosure, a pair of locking protrusions and a pair of locking grooves may be provided.

In the other embodiment of the present disclosure, the first elastic member may include a first extension portion configured to contact a guide surface disposed to be inclined on one side of the cartridge, and become elastically deformed.

In the other embodiment of the present disclosure, the first elastic member may include a seating portion configured to be seated on the first jaw, and a second extension portion extending in a curved shape from the seating portion, and having a portion configured to contact the second jaw.

In the other embodiment of the present disclosure, the first extension portion may be disposed to be inclined such that a portion of the first extension portion forms a predetermined angle with respect to the seating portion.

In the other embodiment of the present disclosure, the second extension portion may be disposed between the second jaw and the working member and is configured to restrict rotation of the second jaw.

In the other embodiment of the present disclosure, a pair of first extension portions and a pair of second extension portions may be provided and arranged on opposite sides of the main body of the working member.

In the other embodiment of the present disclosure, the first jaw may include a first groove arranged at the distal end and corresponding to a coupling protrusion provided in the cartridge.

The present disclosure also relates to a surgical instrument including an end tool rotatable in at least one direction, the end tool which may include a jaw unit having a first jaw configured to accommodate a cartridge, and a second jaw facing the first jaw, and a working member configured to be movable in a lengthwise direction of the first jaw, and a cartridge configured to be mounted on the end tool, the cartridge which may include a housing accommodating a plurality of staples, a wedge configured to eject the plurality of staples while moving from a proximal side to a distal side of the housing as the working member moves, and second elastic members disposed in the housing and having deforming portions configured to be elastically deformable, the second elastic members configured to restrict a movement of the working member based on a position of the wedge.

In another embodiment of the present disclosure, the second elastic members may include a pair of second elastic members, and the deforming portions may be configured to provide restoring forces toward each other.

In the other embodiment of the present disclosure, the deforming portions of the pair of second elastic members may be disposed to cross each other when the wedge deviates from an initial position.

In the other embodiment of the present disclosure, the housing may include second grooves to fix the second elastic members, and the second elastic members may further include fixing portions extending in a curved shape from the deforming portions, and inserted into the second grooves, respectively.

In the other embodiment of the present disclosure, the wedge may include a base plate, a guide plate disposed to protrude from the base plate, and release plates disposed on the base plate and spaced apart from each other on opposite sides of the guide plate, and form a pair of first gaps.

In the other embodiment of the present disclosure, when the wedge is positioned at an initial position, the second elastic members may be disposed in the pair of first gaps, respectively.

In the other embodiment of the present disclosure, when the wedge is positioned at an initial position, the second elastic members may be disposed with the deforming portions spaced apart from each other by a predetermined distance by the guide plate of the wedge.

In the other embodiment of the present disclosure, in the second elastic member, an end of the deforming portion may be formed as a curved surface.

The present disclosure also relates to a cartridge for a surgical instrument, the surgical instrument including an end tool rotatable in at least one direction and includes a working member movable in a lengthwise direction, the cartridge including a housing accommodating a plurality of staples, a wedge configured to eject the plurality of staples while moving from a proximal side to a distal side of the housing as the working member moves, and second elastic members disposed in the housing and having deforming portions configured to be elastically deformable, the second elastic members configured to restrict a movement of the working member based on a position of the wedge.

In another embodiment of the present disclosure, the second elastic members may be provided as a pair, and the deforming portions may provide restoring forces toward each other.

In the other embodiment of the present disclosure, the deforming portions of the pair of second elastic members may be formed to cross each other in response to the wedge deviating from an initial position.

In the other embodiment of the present disclosure, the housing may include second grooves to fix the second elastic members, and the second elastic members may further include fixing portions that are curved and extend from the deforming portions, and are inserted into the second grooves, respectively.

In the other embodiment of the present disclosure, the wedge may include a base plate, a guide plate formed to protrude from the base plate, and release plates that are arranged in the base plate to be spaced apart from each other on opposite sides of the guide plate, and form a pair of first gaps.

In the other embodiment of the present disclosure, in response to the wedge being arranged at an initial position, the second elastic members may be arranged in the pair of first gaps, respectively.

In the other embodiment of the present disclosure, in response to the wedge being arranged at an initial position, the second elastic members may be arranged such that the deforming portions are spaced apart from each other by a certain distance by the guide plate of the wedge.

In the other embodiment of the present disclosure, in the second elastic member, an end of the deforming portion may be formed as a curved surface.

Other aspects, features, advantages other than those described above will become apparent from the following drawings, claims, and detailed description of the present disclosure.

BRIEF DESCRIPTION OF THE DRAWINGS

The above and other aspects, features, and advantages of certain embodiments of the disclosure will be more apparent from the following description taken in conjunction with the accompanying drawings.

DETAILED DESCRIPTION

Figure 1:
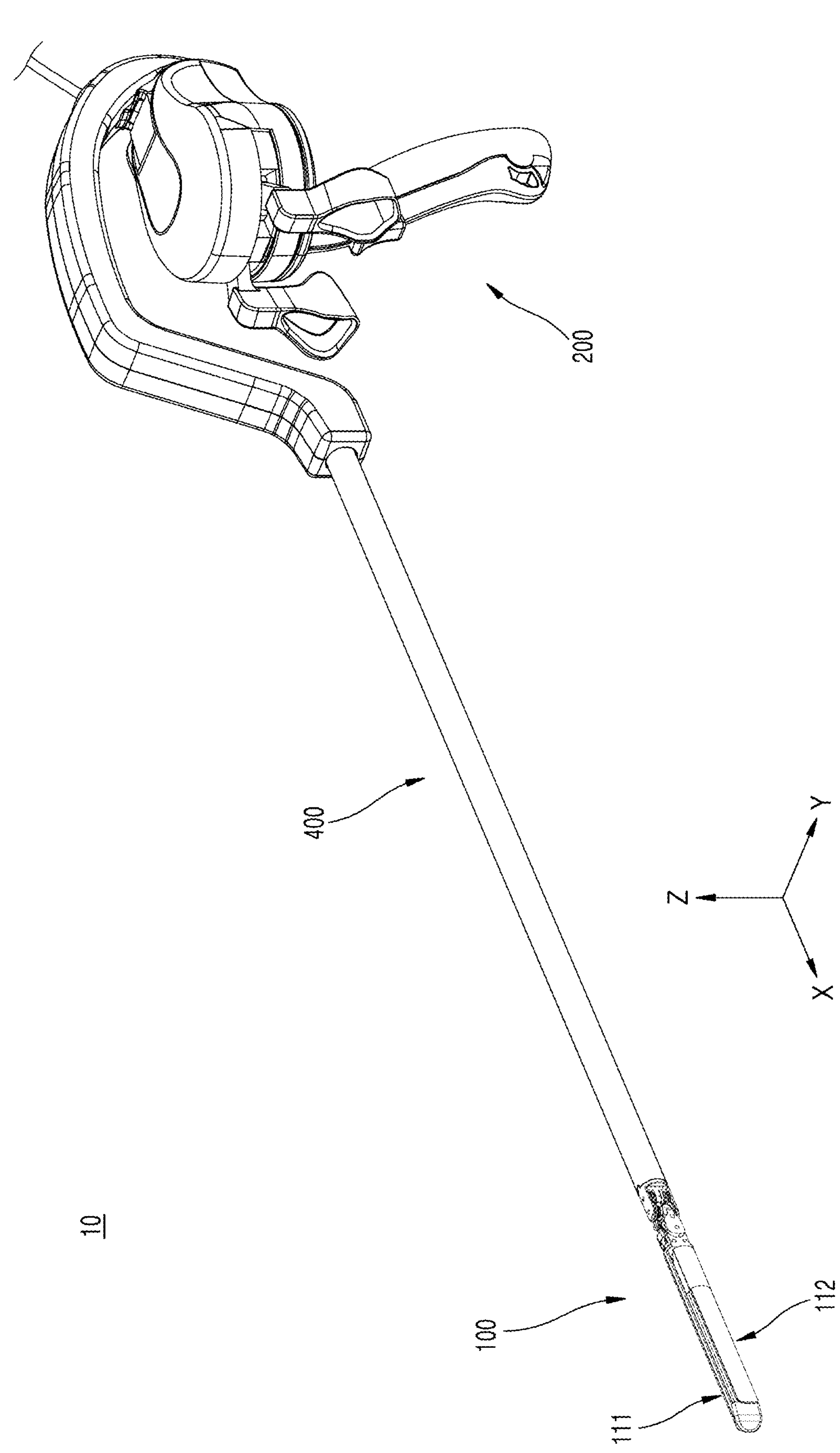
FIG. 1 is a perspective view illustrating a surgical instrument according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term “and/or” includes any and all combinations of one or more of the associated listed items. Expressions such as “at least one of,” when preceding a list of elements, modify the entire list of elements and do not modify the individual elements of the list.

Hereinafter, embodiments will be described in detail with reference to the accompanying drawings, and the same or corresponding components will be denoted by the same reference numerals when described with reference to the accompanying drawings, and thus their descriptions that are already provided will be omitted.

As the embodiments may be variously modified, particular embodiments will be illustrated in the drawings and described in detail in the detailed description. The effects and features of the present embodiments and methods of achieving them will become clear from detail descriptions provided below along with the drawings. However, the embodiments are not limited to the descriptions below, and may be implemented in various forms.

In describing the present disclosure, detailed explanations of the related art are omitted when it is deemed that they may unnecessarily obscure the gist of the present disclosure.

In the following embodiments, the singular expression also includes the plural meaning as long as it is not inconsistent with the context. In the following embodiments, terms such as “first” or “second” may be used to describe various elements, but the elements should not be limited by the terms. These terms are used only to distinguish one element from another.

In the following embodiments, the terms “comprises,” “includes,” “has”, and the like used herein specify the presence of stated features or components, but do not preclude the presence or addition of one or more other features or components.

In the following embodiments, when a unit, region, or component is referred to as being “on” another unit, region, or component, it may be directly or indirectly on the other unit, region, or component, that is, one or more intervening units, regions, or components may be present therebetween.

In the following embodiments, when a component is referred to as being “connected to” or “coupled to” another component, the component may be directly connected to or in direct contact with the other component or intervening components may be present therebetween, unless clearly defined otherwise in the context.

For convenience of description, the magnitude of components in the drawings may be exaggerated or reduced. For example, each component in the drawings is illustrated to have an arbitrary size and thickness for ease of description, and thus the embodiments are not limited to the drawings.

Structure of Surgical Instrument

Figure 2:
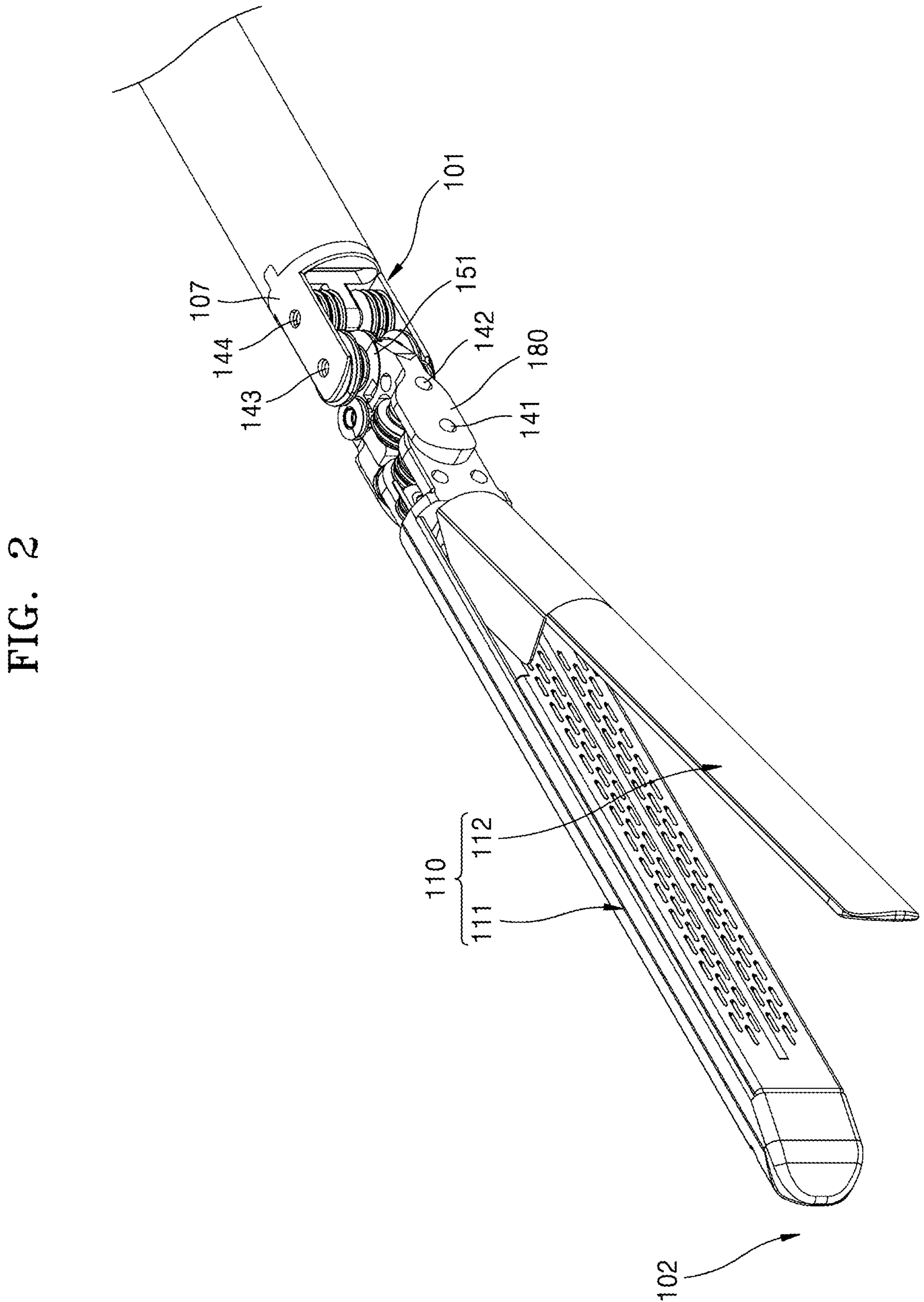
FIG. 2 is a perspective view illustrating an end tool of the surgical instrument of FIG. 1.
Figure 3:
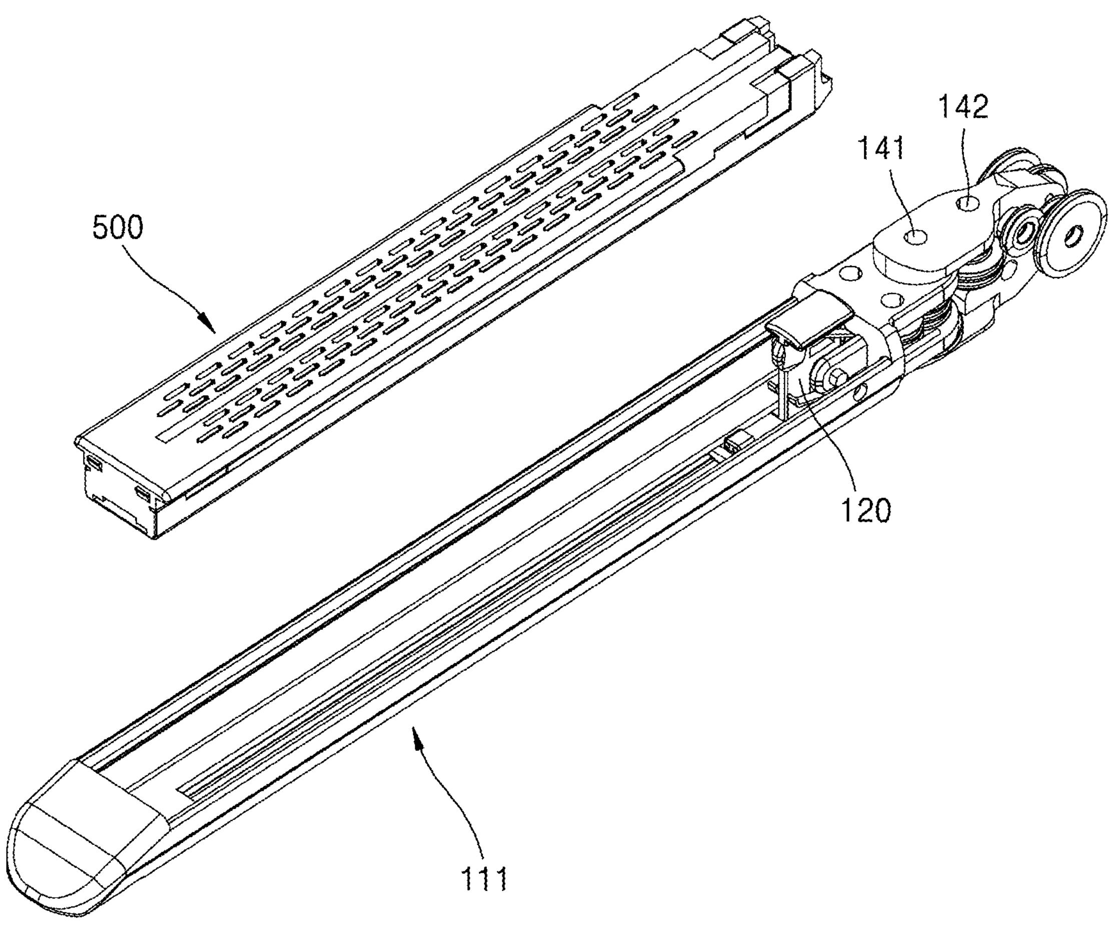
FIG. 3 is an exploded perspective view illustrating a partial configuration of the surgical instrument of FIG. 1.
Figure 4:
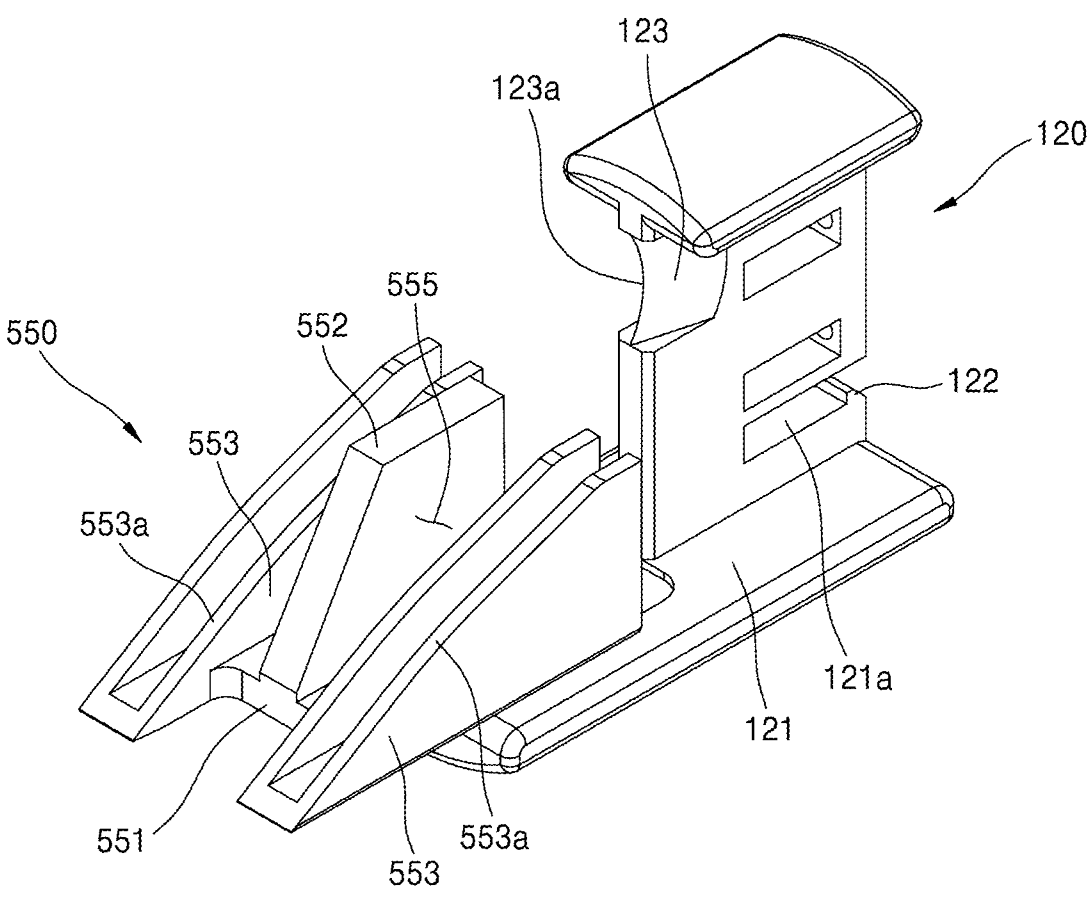
FIG. 4 is an enlarged perspective view illustrating a working member of FIG. 3.
Figure 5:
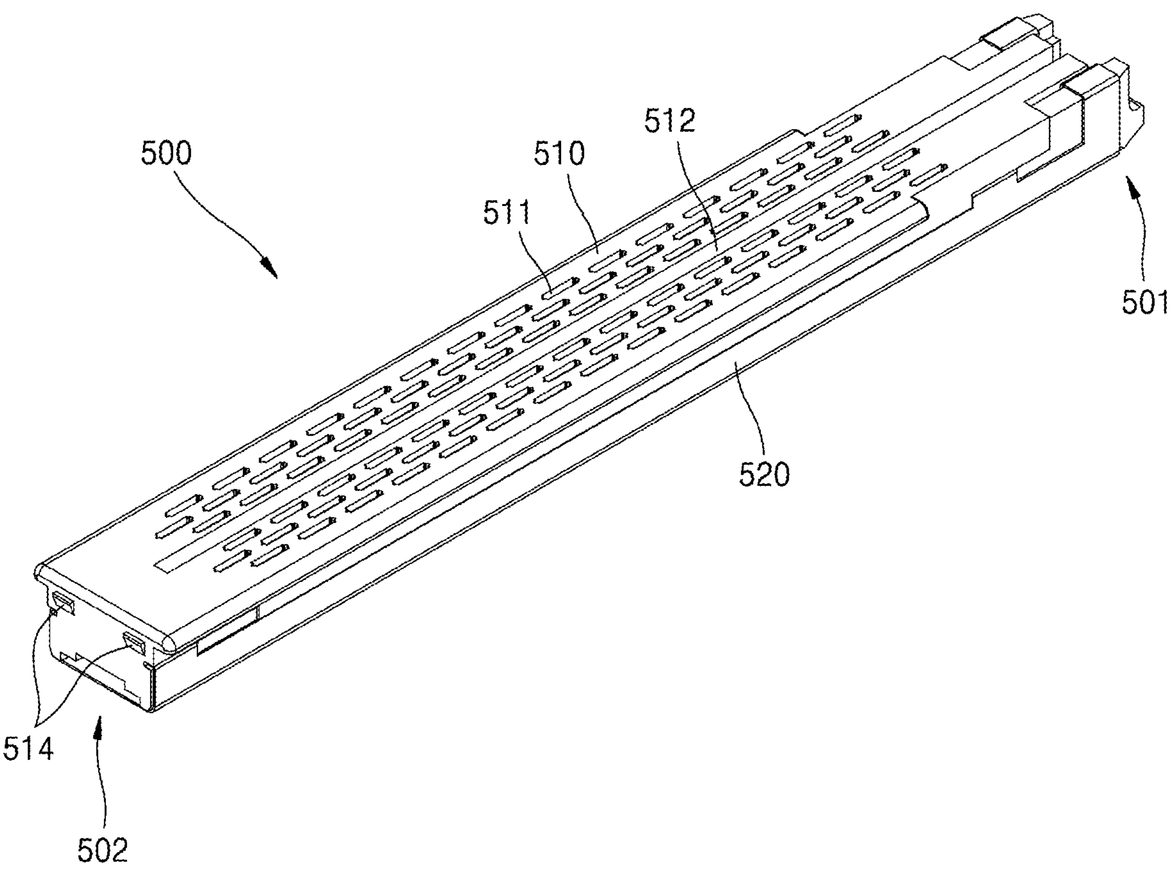
FIGS. 5 and 6 are perspective views illustrating a cartridge of FIG. 3.
Figure 6:
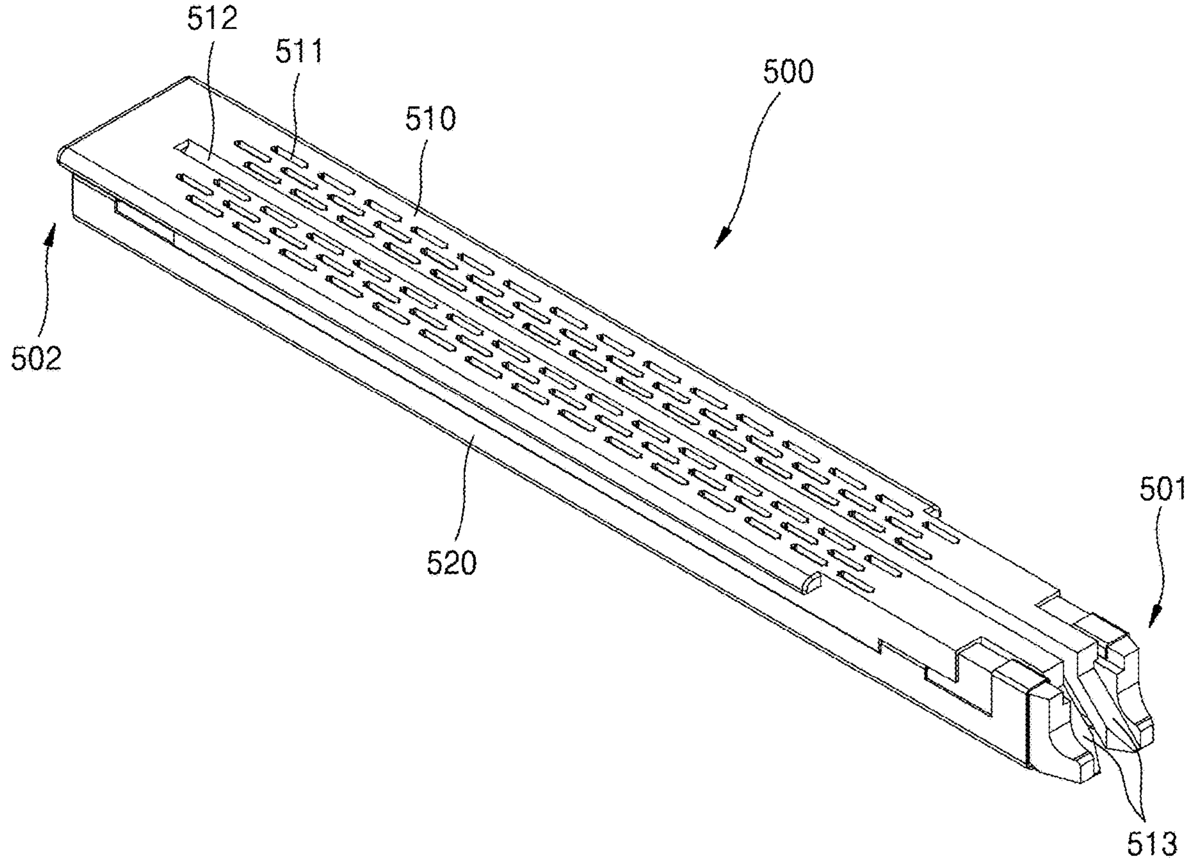
Figure 7:
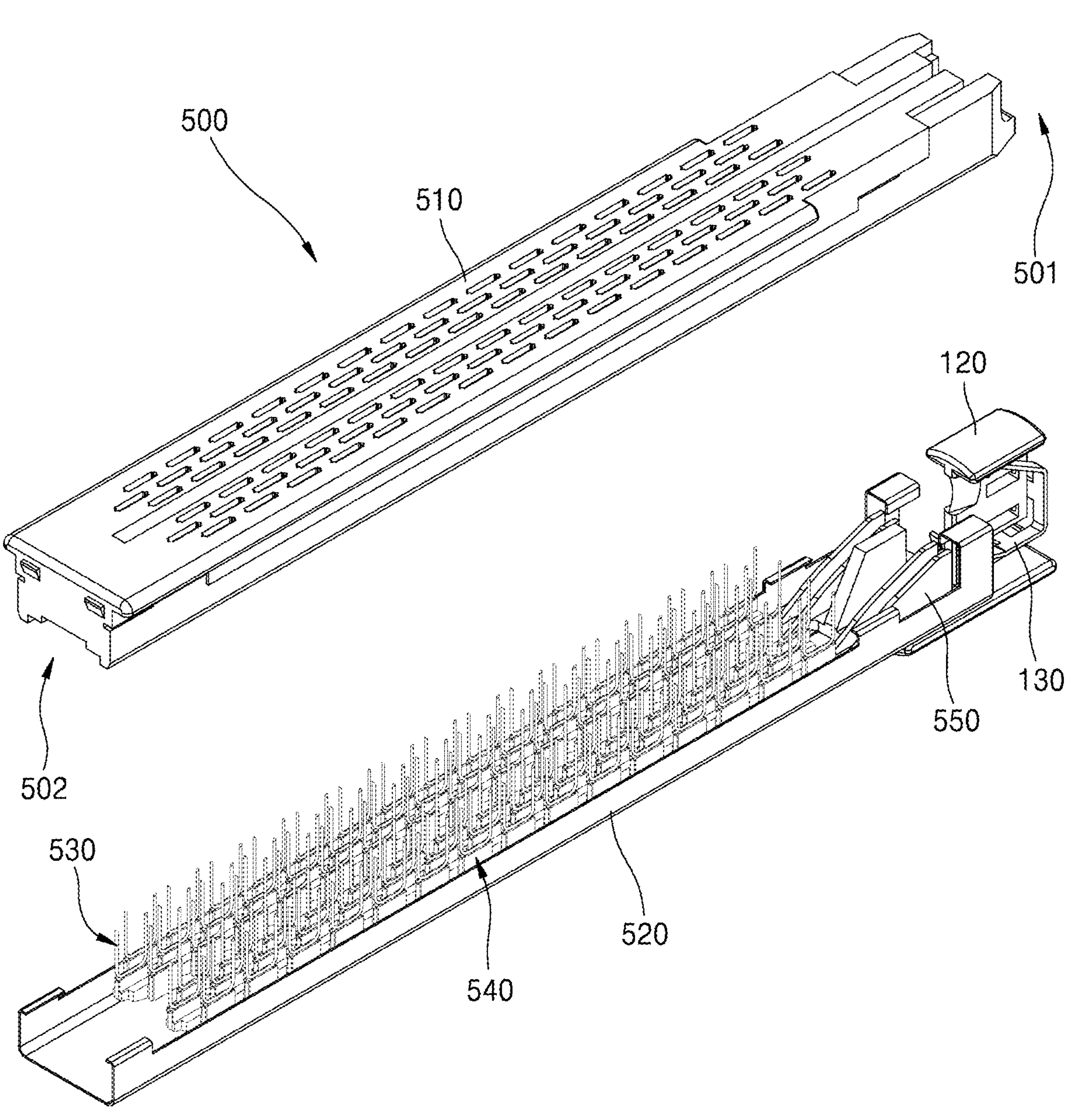
FIG. 7 is an exploded perspective view illustrating a partial configuration of the cartridge of FIG. 3.
Figure 8:
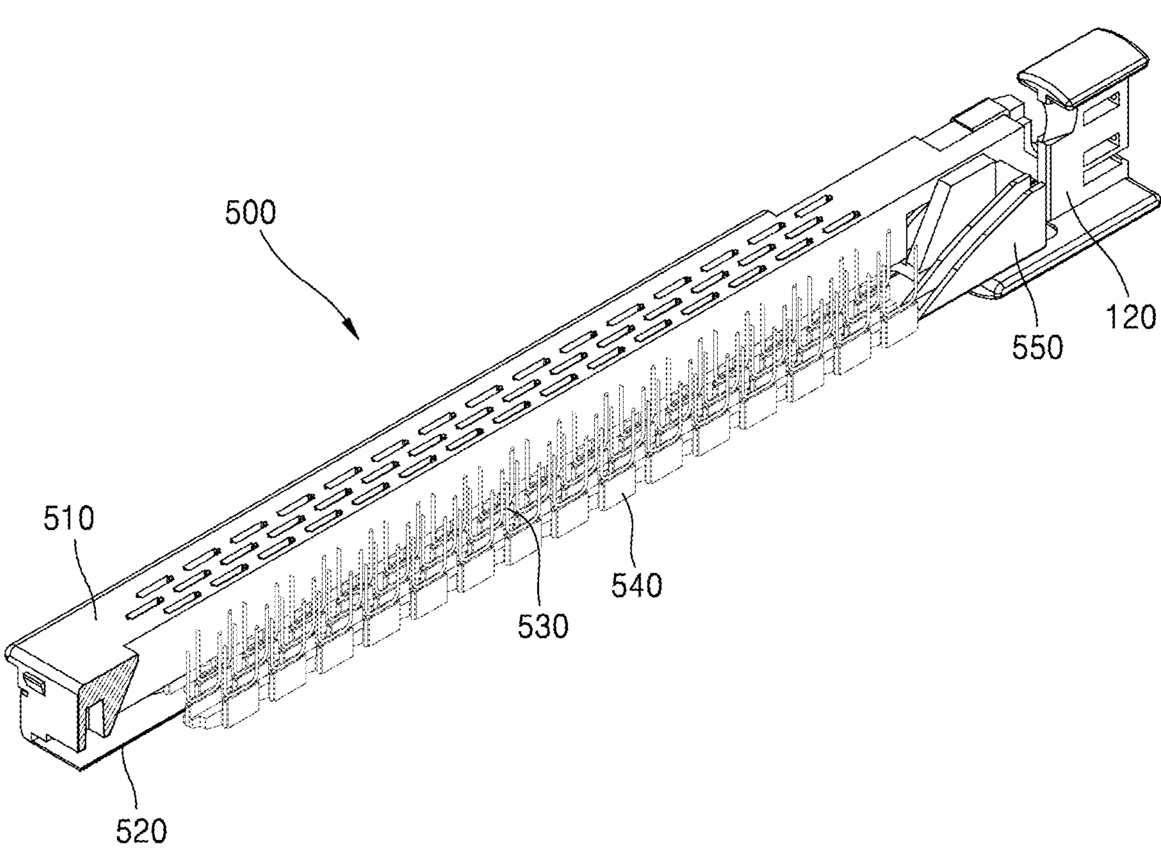
FIG. 8 is a cross-sectional view illustrating a partial configuration of the cartridge of FIG. 3.
Figure 9:
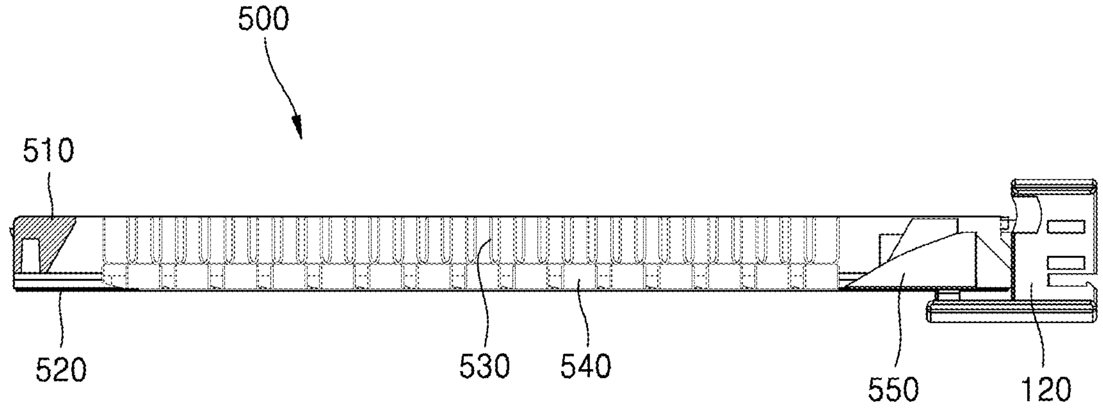
FIG. 9 is a side cross-sectional view illustrating a partial configuration of the cartridge of FIG. 3.

FIG. 1 is a perspective view illustrating a surgical instrument 10 according to an embodiment of the present disclosure, and FIG. 2 is a perspective view illustrating an end tool 100 of the surgical instrument 10 of FIG. 1. FIG. 3 is a perspective view illustrating a partial configuration of the surgical instrument 10 of FIG. 1, and FIG. 4 is an enlarged perspective view illustrating a working member 120 of FIG. 3. FIGS. 5 and 6 are perspective views illustrating a cartridge 500 of FIG. 3. FIG. 7 is an exploded perspective view illustrating a partial configuration of the cartridge 500 of FIG. 3, FIG. 8 is a perspective cross-sectional view illustrating a partial configuration of the cartridge 500 of FIG. 3, and FIG. 9 is a side cross-sectional view illustrating a partial configuration of the cartridge 500 of FIG. 3.

Referring to FIG. 1, the surgical instrument 10 according to an embodiment of the present disclosure may include the end tool 100, a manipulation part 200, a power transmission part (not shown), and a connection part 400.

Here, the connection part 400 may be formed in the shape of a hollow shaft, to accommodate therein one or more wires and electric wires. As the manipulation part 200 is coupled to one end of the connection part 400, and the end tool 100 is coupled to the other end, the connection part 400 may serve to connect the manipulation part 200 to the end tool 100.

In addition, the manipulation part 200 may be formed at one end of the connection part 400 and may include an interface that may be directly manipulated by a doctor, for example, an interface in the shape of a pincer, a stick, a lever, etc. When the doctor manipulates the interface, the end tool 100, which is connected to the interface to be inserted into a patient’s body, operates in a certain manner to perform surgery.

Here, although FIG. 1 illustrates that the manipulation part 200 is formed in the shape of a handle that may be rotated while fingers are inserted therein, the present disclosure is not limited thereto, and various types of manipulation parts that may be connected to the end tool 100 to manipulate the end tool 100 may be possible.

The end tool 100 may be formed at the other end of the connection part 400 and may be inserted into a surgical site to perform a motion necessary for surgery. As an example of the end tool 100, a jaw unit 110 for performing a grip motion as illustrated in FIG. 2 may be used. However, the concept of the present disclosure is not limited thereto, and various other surgical instruments may be used as the end tool 100. For example, a one-armed cautery may be used as the end tool. As the end tool 100 is connected to the manipulation part 200 by the power transmission part (not shown), the end tool 100 may receive a driving force of the manipulation part 200 through the power transmission part (not shown) to perform motions required for surgery, such as a grip motion, a cutting motion, or a suturing motion.

Here, the end tool 100 of the surgical instrument 10 according to an embodiment of the present disclosure may be formed to be rotatable in at least one direction, and for example, the end tool 100 may be formed to perform a pitch motion around the Y-axis of FIG. 1 and simultaneously perform a yaw motion and an actuation motion around the Z-axis of FIG. 1.

In addition, the power transmission part (not shown) may serve to connect the manipulation part 200 to the end tool 100 to transmit a driving force of the manipulation part 200 to the end tool 100, and may include a plurality of wires, pulleys, links, joints, gears, and the like.

In describing the present disclosure, a portion close to the user side, that is, a portion closer to the manipulation part 200, will be referred to as a proximal end, and a portion farther from the user side will be referred to as a distal end.

For example, referring to FIGS. 1 and 2, a portion of the end tool 100 closer to the manipulation part 200 is defined as a proximal end 101 of the end tool 100, and a portion far from the manipulation part 200 is defined as a distal end 102 of the end tool 100. In other words, it may be described that the proximal end 101 of the end tool 100 is the portion closer to the connection part 400, and the distal end 102 of the end tool 100 is the portion farther from the connection part 400.

Similarly, referring to FIG. 1 and FIG. 5, a portion of the cartridge 500 closer to the manipulation part 200 is defined as a proximal end 501 of the cartridge 500, and a portion farther from the manipulation part 200, that is, a portion closer to the end of the end tool 100 is defined as a distal end 502 of the cartridge 500. In other words, it may be described that the proximal end 501 of the cartridge 500 is the portion closer to the connection part 400, and the distal end 502 of the cartridge 500 is the portion farther from the connection part 400.

In addition, in describing the present disclosure, movement in the direction from the proximal end of the end tool 100 toward the distal end will be referred to as forward movement, and movement in the direction from the distal end toward the proximal end will be referred to as backward movement.

For example, the working member 120 to be described below may move forward in the direction from the proximal end 101 of the end tool 100 toward the distal end 102, and may move backward in the direction from the distal end 102 of the end tool 100 toward the proximal end 101. In addition, a wedge 550 to be described below may be moved forward in the direction from the proximal end 501 of the cartridge 500 toward the distal end 502, by the working member 120.

Detailed Structure of End Tool

Hereinafter, the end tool 100 of the surgical instrument 10 of FIG. 1 will be described in more detail.

Referring to FIGS. 1 to 4, the end tool 100 according to an embodiment of the present disclosure includes the jaw unit 110 and the working member 120.

The end tool 100 includes the jaw unit 110 for performing a grip motion. The jaw unit 110 may include a first jaw 111 and a second jaw 112, wherein the first jaw 111 may accommodate the cartridge 500, and the second jaw 112 may be arranged to face the first jaw 111.

The working member 120 may be arranged in the first jaw 111, and may move linearly in the lengthwise direction of the first jaw 111.

The working member 120 may have one side in contact with the wedge 550 that is arranged inside the cartridge 500. The working member 120 may perform a stapling motion by moving forward while pushing the wedge 550 arranged inside the cartridge 500.

The working member 120 may include a blade 123. The working member 120 has the blade 123 on one side thereof, and an edge portion **123*a* may be sharply formed in one area of the blade 123** to cut tissue.

The working member 120 may cut tissue positioned between the first jaw 111 and the second jaw 112 while at least a portion of the edge portion **123*a* of the blade 123 is drawn out of the first jaw 111 and the cartridge 500. The edge portion 123*a* of the blade 123 may always be drawn out of the first jaw 111. Alternatively, the edge portion 123*a* of the blade 123 may normally be accommodated in the first jaw 111 or the cartridge 500, and may be drawn out of the first jaw 111 only when the working member 120** moves in the lengthwise direction.

As such, the working member 120 may perform stapling and cutting motions while moving linearly in the lengthwise direction of the first jaw 111. Here, the method in which the working member 120 moves linearly, that is, moves forward in the direction from the proximal end 101 of the end tool 100 toward the distal end 102, or moves backward in the direction from the distal end 102 of the end tool 100 toward the proximal end 101, may vary.

For example, the working member 120 may be linearly moved by a reciprocating assembly (not shown) that performs a reciprocating linear motion by transforming a rotational motion of a pulley to the reciprocating linear motion of the reciprocating assembly (not shown). Alternatively, a wire may be directly fixed to the working member 120 such that the working member 120 linearly moves through a structure using a pulley and a wire. However, the technical idea of the present disclosure is not limited thereto, and various mechanisms for linearly moving the working member 120 may be used. Hereinafter, for convenience of description, an example will be described in which the working member 120 is linearly moved by using the reciprocating assembly (not shown) as described above.

The end tool 100 according to an embodiment of the present disclosure may include pulleys associated with rotational motions of the first jaw 111 and the second jaw 112.

Here, although the drawings illustrate that the pulleys facing each other are arranged in parallel to each other, the present disclosure is not limited thereto, and the pulleys may be formed in various positions and sizes suitable for the configuration of the end tool.

In addition, the end tool 100 according to an embodiment of the present disclosure may include an end tool hub 180 and a pitch hub 107.

A first rotation shaft 141 and a second rotation shaft 142 may be inserted through the end tool hub 180, and the end tool hub 180 may accommodate therein at least portions of pulleys that are axially coupled to the first rotation shaft 141.

In addition, the end tool hub 180 may accommodate therein at least portions of pulleys that are axially coupled to the second rotation shaft 142.

In addition, a pulley 151 serving as an end tool pitch pulley may be formed at one end of the end tool hub 180. The pulley 151 may be formed with the end tool hub 180 as one body. That is, a disk-shaped pulley may be formed at one end of the end tool hub 180, and a groove around which a wire may be wound may be formed on an outer circumferential surface of the end tool hub 180. Alternatively, the pulley 151 may be formed as a separate member from the end tool hub 180 and then coupled to the end tool hub 180. A wire (not shown) may be coupled to the pulley 151 serving as an end tool pitch pulley, and a pitch motion may be performed as the pulley 151 rotates around a third rotation shaft 143.

The third rotation shaft 143 and a fourth rotation shaft 144, which will be described below, may be inserted through the pitch hub 107, and the pitch hub 107 may be axially coupled to the end tool hub 180 (and the pulley 151) by the third rotation shaft 143. Thus, the end tool hub 180 and the pulley 151 may be formed to be rotatable around the third rotation shaft 143 with respect to the pitch hub 107.

In addition, the pitch hub 107 may accommodate therein at least portions of pulleys that are axially coupled to the third rotation shaft 143. In addition, the pitch hub 107 may accommodate therein at least portions of pulleys that are axially coupled to the fourth rotation shaft 144.

Here, the first rotation shaft 141 may function as an end tool jaw pulley rotation shaft, the second rotation shaft 142 may function as an end tool jaw auxiliary pulley rotation shaft, the third rotation shaft 143 may function as an end tool pitch rotation shaft, and the fourth rotation shaft 144 may function as an end tool pitch auxiliary rotation shaft of the end tool 100. One or more pulleys may be fitted into each of the first rotation shaft 141 to the fourth rotation shaft 144.

Here, although not illustrated in the drawings, a pulley serving as an end tool jaw pulley may be fixedly coupled to each of the first jaw 111 and the second jaw 112, to rotate together with the jaw. A yaw motion and an actuation motion of the end tool 100 are performed as the pulleys rotate. That is, when the pulleys of the respective jaws rotate in the same direction around the first rotation shaft 141, the yaw motion is performed, and when the pulleys of the respective jaws rotate in opposite directions around the first rotation shaft 141, the actuation motion is performed.

Here, the jaw and the pulleys may be formed as separate members and then coupled to each other, or may be formed as one body.

Detailed Structure of Cartridge

Hereinafter, the cartridge 500 of the surgical instrument 10 of FIG. 1 will be described in more detail.

Referring to FIGS. 5 to 9, the cartridge 500 is formed to be mountable to and dismountable from the first jaw 111, and includes therein a plurality of staples 530 so as to perform suturing and cutting of tissue. Here, the cartridge 500 may include a cover 510, a housing 520, staples 530, release members 540, a wedge 550, and a reciprocating assembly (not shown).

The housing 520 may form the exterior of the cartridge 500, and may be formed in the shape of a hollow box with one side (upper surface) removed, to accommodate therein the staples 530, the release member 540, the wedge 550, and the reciprocating assembly (not shown). Here, the housing 520 may be formed to have a substantially 'U'-shaped cross-section.

The cover 510 is formed to cover an upper portion of the housing 520. The cover 510 may have formed therein staple holes 511 through which the plurality of staples 530 may be ejected to the outside. The plurality of staples 530, which are accommodated in the housing 520 before a stapling operation, may be pushed up by the wedge 550 during a stapling motion. Accordingly, stapling is performed as the plurality of staples 530 pass through the staple holes 511 of the cover 510 and are then released from the cartridge 500.

In addition, the cover 510 may have a slit 512 formed in the lengthwise direction thereof. The blade 123 of the working member 120 may protrude out of the cartridge 500 through the slit 512. The blade 123 of the working member 120 may cut stapled tissue while passing along the slit 512.

The plurality of staples 530 may be arranged inside the housing 520. As the working member 120, which will be described below, linearly moves in one direction, the plurality of staples 530 may be sequentially pushed up from the inside of the housing 520 to the outside, thereby performing suturing, that is, stapling. Here, the material of the staples 530 may include titanium, stainless steel, etc.

In addition, the release member 540 may be further arranged between the housing 520 and the staple 530. In other words, the staple 530 may be arranged on the release member 540. In this case, the wedge 550 may linearly move in one direction to push up the release member 540, and the release member 540 may push up the staple 530.

It may be described that the wedge 550 pushes up the staple 530, including cases in which the wedge 550 directly pushes up the staple 530, and cases in which the wedge 550 pushes up the release member 540 such that the release member 540 pushes up the staple 530 (i.e., cases in which the wedge 550 indirectly pushes up the staple 530).

As the working member 120 moves forward in the direction from the proximal end 101 of the end tool 100 toward the distal end 102, the wedge 550 may move forward together with the working member 120. The wedge 550 may be arranged inside the housing 520 to have one side in contact with the working member 120 such that the working member 120 may push the wedge 550, and thus, the wedge 550 move forward in the direction from the proximal end 501 of the cartridge 500 toward the distal end 502, together with the working member 120.

The wedge 550 may be arranged inside the housing 520. The wedge 550 may move linearly together with the working member 120 to perform a stapling motion while moving forward in the extension direction of the connection part 400. That is, the wedge 550 may be arranged inside the housing (520) to have one side in contact with the working member 120 such that the working member 120 may move forward together with the wedge 550 in the direction from the proximal end 501 of the cartridge 500 toward the distal end 502, while pushing the wedge 550.

As such, the wedge 550 may be formed to be able to sequentially come into contact with the release members 540 or the plurality of staples 530, and may serve to sequentially push up the staples 530 to withdraw them out of the cartridge 500 while moving toward the distal end 502 together with the working member 120.

Stapling Motion of Surgical Instrument

Figure 10A:
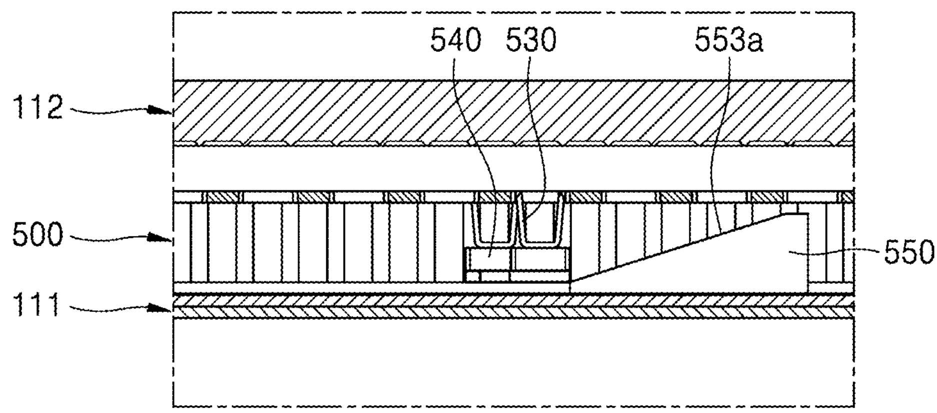
FIGS. 10A-10C are side cross-sectional views illustrating each section of a stapling motion of the surgical instrument of FIG. 1.
Figure 10B:
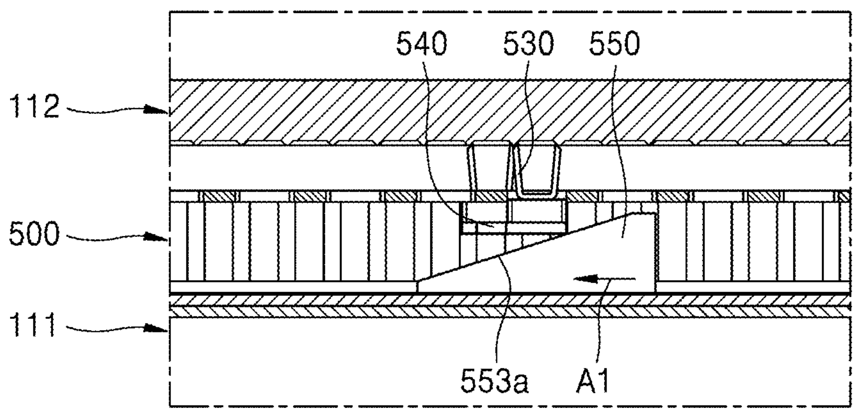
Figure 10C:
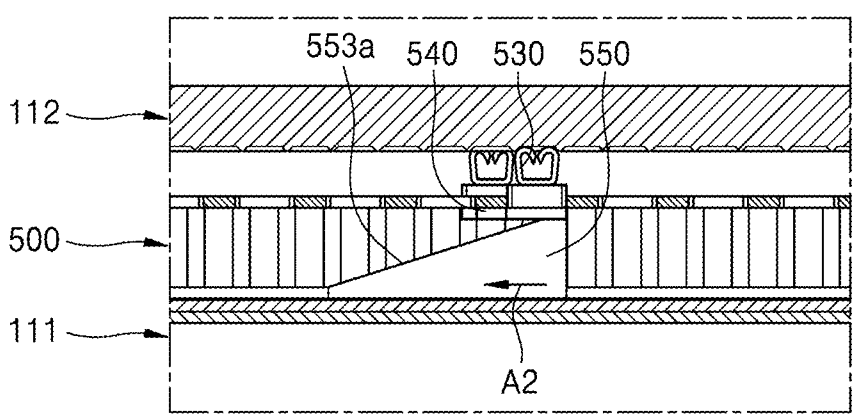
Figure 11:
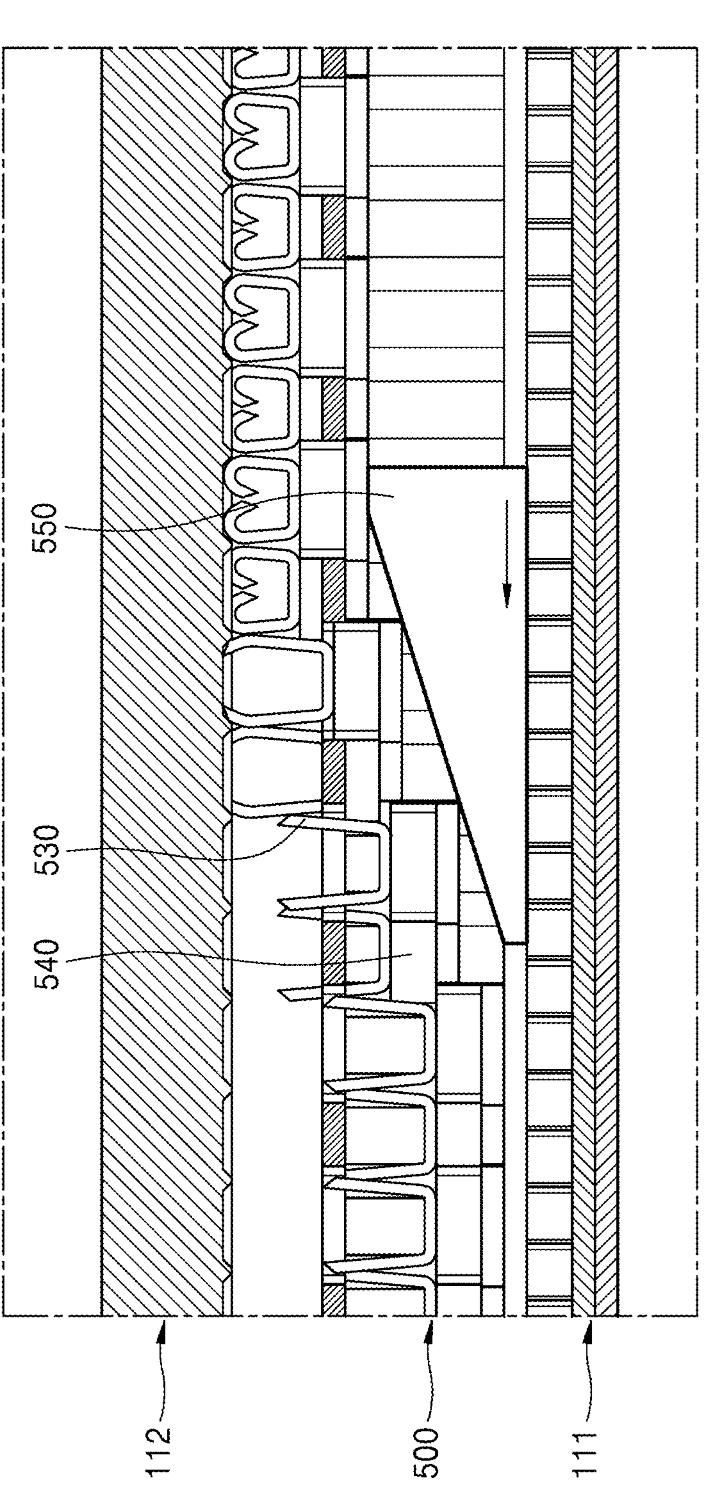
FIG. 11 is a side cross-sectional view illustrating an overall stapling motion of the surgical instrument of FIG. 1.

FIG. 10 is a side cross-sectional view illustrating each section of a stapling motion of the surgical instrument 10 of FIG. 1, and FIG. 11 is a side cross-sectional view illustrating an overall stapling motion of the surgical instrument 10 of FIG. 1.

Referring to FIGS. 10 and 11, in a state as illustrated in (a) of FIG. 10, as the wedge 550 moves in the direction of arrow A1 of (b) of FIG. 10, an inclined surface 553*a* of the wedge 550 pushes up the release member 540, and the release member 540 pushes up a lower side of the staple 530. This causes the staple 530 to be ejected out of the first jaw 111 and the cartridge 500.

In this state, when the wedge 550 moves further in the direction of arrow A2 in (c) of FIG. 10, the ejected staple 530 is continuously pushed up by the wedge 550 while being in contact with an anvil (not shown) of the second jaw 112, both ends of the staple 530 are curved, and thus, stapling is performed.

As the above motions are continuously performed, stapling is sequentially performed from the staple 530 on the side of the proximal end 501 to the staple 530 on the side of the distal end 502 among the plurality of staples 530, as illustrated in FIG. 11.

In summary, in the surgical instrument 10 according to an embodiment of the present disclosure, when the working member 120 moves toward the distal end 102 of the end tool 100, the wedge 550 moves together with the working member 120 toward the distal end 502 of the cartridge 500 and ejects the staple 530 out of the cartridge 500 while the blade 123 of the working member 120 cuts body tissue. Here, it may be described that, the surgical instrument 10 according to an embodiment of the present disclosure simultaneously performs suturing and cutting of body tissue interposed between the first jaw 111 and the second jaw 112.

In addition, in a case in which the cartridge 500 is not mounted on the first jaw 111 or in a case in which the cartridge 500 that has already performed a stapling motion and thus has no staples 530 arranged therein is mounted on the first jaw 111, when the working member 120 moves forward toward the distal end 102, only cutting of body tissue is performed and a stapling motion cannot be performed due to the absence of the staples 530. When the body tissue is only cut and not sutured as described above, serious problems such as excessive bleeding or leakage of cancer tissue may occur.

Therefore, the need for a lockout system is emerging, capable of preventing the working member 120 from moving forward toward the distal end 102 when the staples 530 are not arranged in the end tool 100.

The present disclosure has been devised to solve this problem, and provides a cartridge for a surgical instrument, which has a lockout system capable of preventing the working member 120 from moving forward in response to the absence of the staples 530 by using several mechanisms to be described below, and a surgical instrument including the cartridge.

First Mechanism of Lockout System

Figure 12:
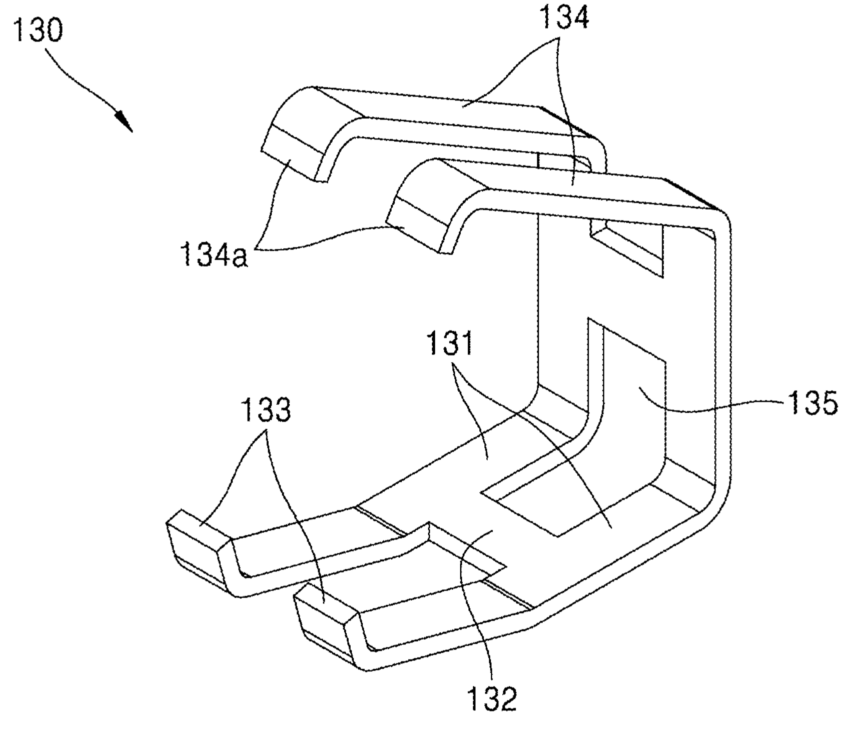
FIG. 12 is an enlarged perspective view illustrating a first elastic member of the end tool of FIG. 2.
Figure 13:
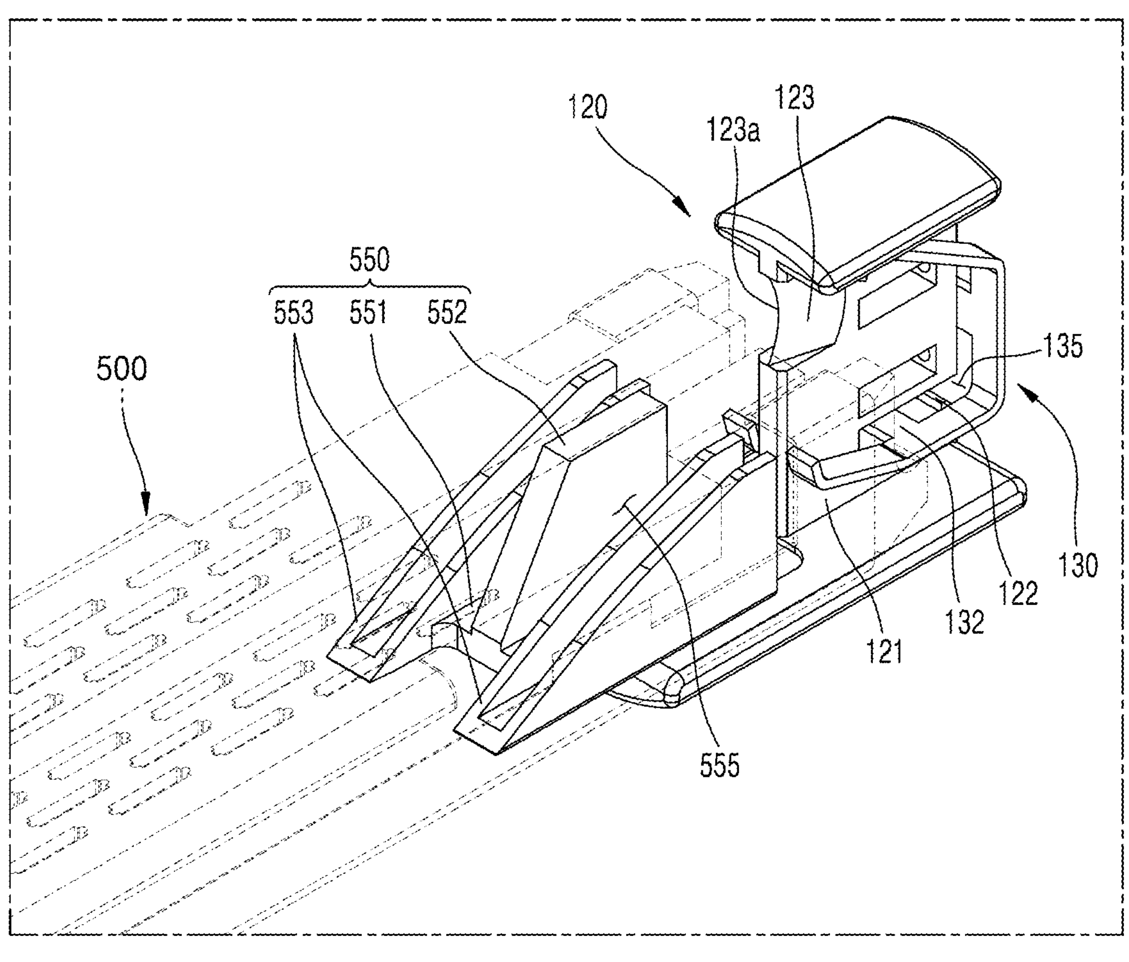
FIG. 13 is a perspective view illustrating a state in which the first elastic member of FIG. 12 is arranged in a first jaw.
Figure 14:
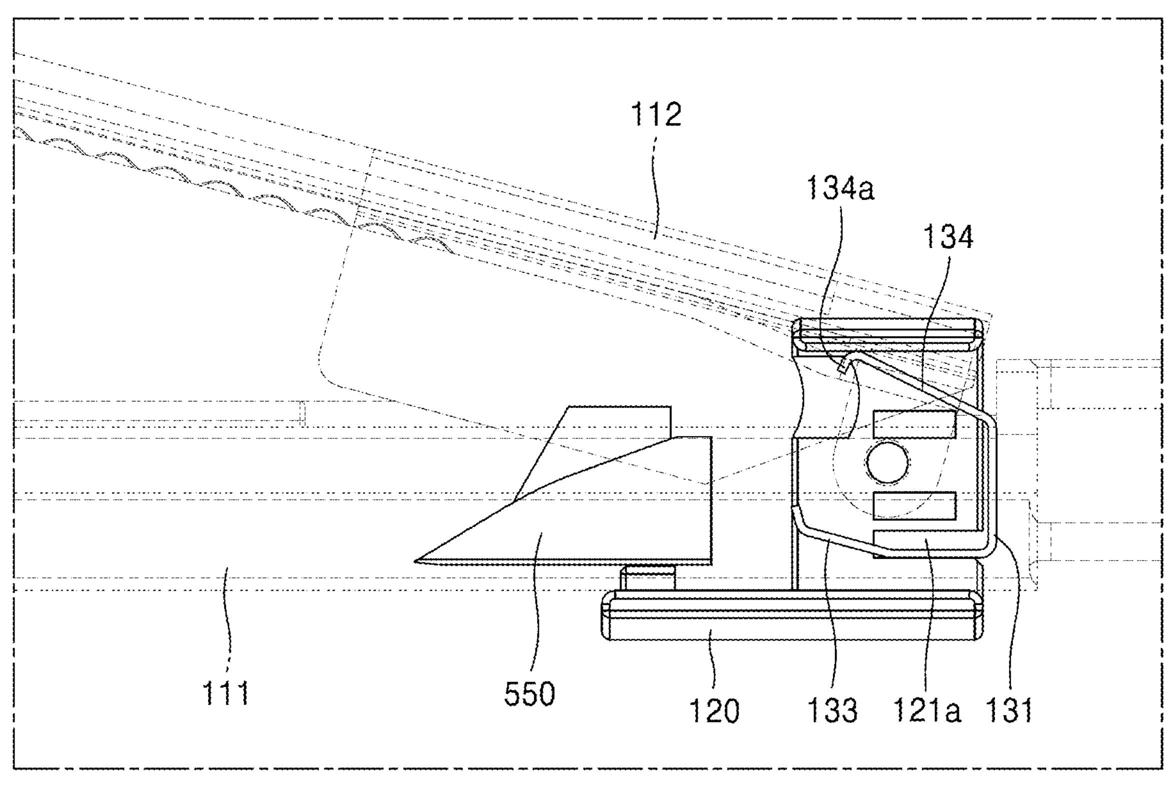
FIG. 14 is a side cross-sectional view illustrating a state in which the first elastic member of FIG. 12 is arranged in a first jaw.
Figure 15:
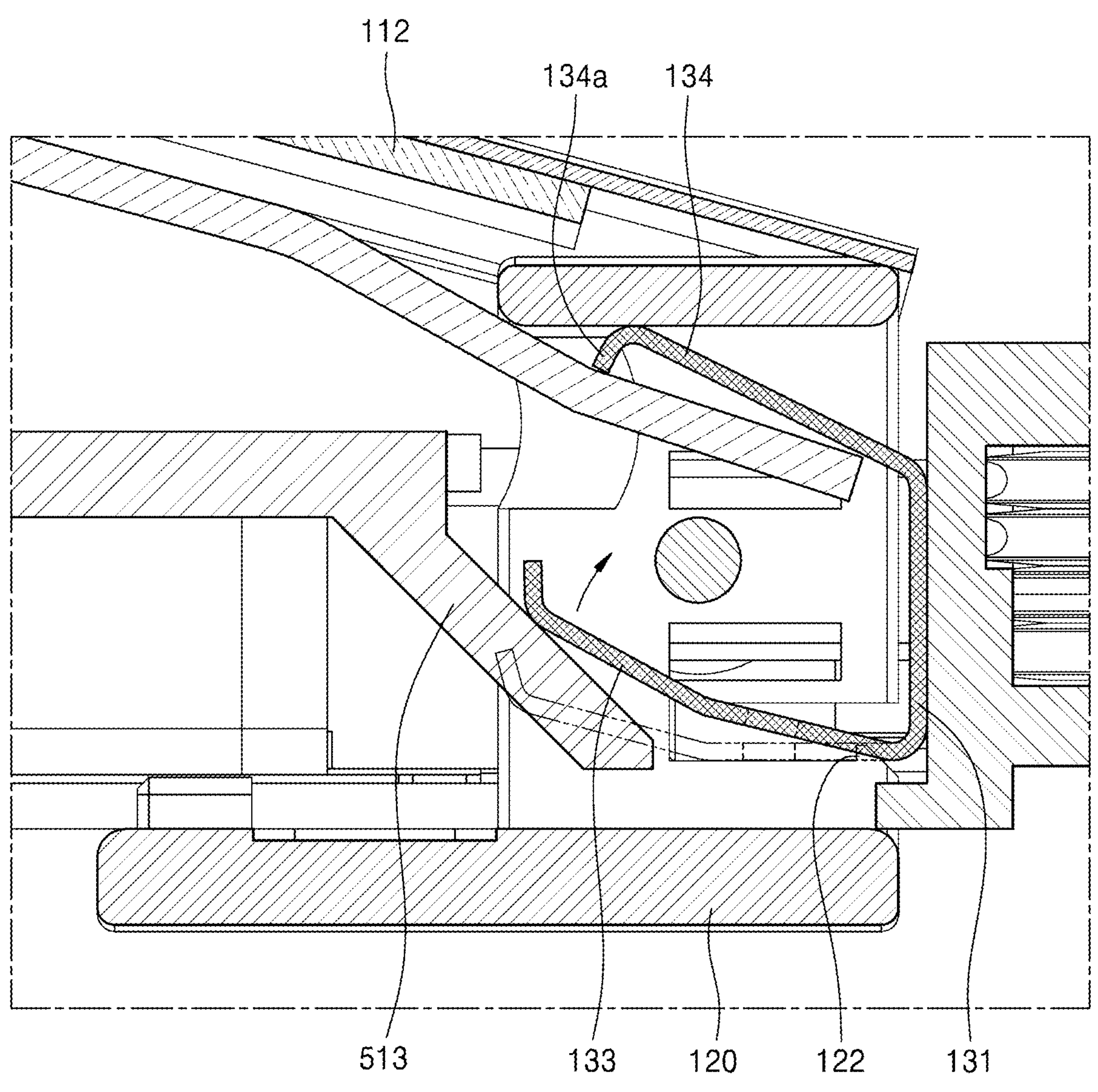
FIG. 15 is a side cross-sectional view illustrating a state in which the first elastic member of FIG. 12 is elastically deformed.

FIG. 12 is an enlarged perspective view illustrating a first elastic member 130 of the end tool 100 of FIG. 2. FIG. 13 is a perspective view illustrating a state in which the first elastic member 130 of FIG. 12 is arranged in the first jaw 111, FIG. 14 is a side cross-sectional view illustrating a state in which the first elastic member 130 of FIG. 12 is arranged in the first jaw 111, and FIG. 15 is a side cross-sectional view illustrating a state in which the first elastic member 130 of FIG. 12 is elastically deformed.

Referring to FIGS. 12 to 15, the end tool 100 of the surgical instrument 10 according to an embodiment of the present disclosure may include the first elastic member 130. The first elastic member 130 may be arranged on the proximal side of the first jaw 111 to restrict the movement of the working member 120 depending on whether the cartridge 500 is accommodated in the first jaw 111.

Hereinafter, a shape of the first elastic member 130 and an arrangement relationship between the first elastic member 130 and the working member 120 according to an embodiment of the present disclosure will be described, and a first mechanism of the lockout system that prevents a forward movement of the working member 120 will be described in detail.

First, referring back to FIG. 4, the working member 120 may include a main body 121 and a locking protrusion 122. The main body 121 may form a base portion of the working member 120, and one side of the main body 121 may come into contact with the wedge 550.

The main body 121 may have a first slit 121*a* formed by cutting a portion thereof. The first slit 121*a* provides a space in which a portion of the first elastic member 130 may be arranged.

The locking protrusion 122 may be formed to protrude from the main body 121 toward the first slit 121*a*. The locking protrusion 122 may engage with the first elastic member 130 arranged in the first slit 121*a*, particularly, with a locking flange 132.

In addition, referring to FIGS. 12 to 14, the first elastic member 130 may be arranged in the first jaw 111, and may be formed to engage with the working member 120 to restrict the forward movement of the working member 120 when the cartridge 500 is not mounted on the first jaw 111.

The first elastic member 130 may include a seating portion 131 and the locking flange 132. A pair of seating portions 131 may be provided, and the locking flange 132 may be arranged to connect the pair of seating portions 131 to each other.

The seating portion 131 of the first elastic member 130 may be seated on the first jaw 111. The seating portion 131 may form a first opening 135 together with the locking flange 132, and when the first elastic member 130 is arranged in the first jaw 111, the locking protrusion 122 of the working member 120 may be positioned in the first opening 135.

That is, the first elastic member 130 may be arranged such that the locking flange 132 is positioned in the first slit 121*a* of the working member 120 and the locking protrusion 122 is positioned in the first opening 135. Through this configuration, the first elastic member 130 may engage with the locking protrusion 122 of the working member 120 so as to restrict the movement of the working member 120 when the cartridge 500 is not mounted on the first jaw 111.

In addition, when the cartridge 500 is mounted on the first jaw 111 as illustrated in FIG. 15, the first elastic member 130 may be elastically deformed to release the restriction on the movement of the working member 120.

The first elastic member 130 may include a first extension portion 133 extending from one side of the seating portion 131. When the cartridge 500 is mounted on the first jaw 111, the first extension portion 133 may come into contact with a guide surface 513 that is formed to be inclined on one side of the cartridge 500.

The first extension portion 133 may be formed to be elastically deformable, such that the cartridge 500 mounted on the first jaw 111 may push up the first extension portion 133. In detail, the first extension portion 133 may be formed in a shape in which a portion is curved at a certain angle with respect to the seating portion 131. As a portion of the first extension portion 133 is formed to have a certain angle with respect to the seating portion 131, an unoccupied space may be formed between the first jaw 111 and the first extension portion 133. The cartridge 500 may be easily mounted on the first jaw 111 through the unoccupied space while pushing up the first extension portion 133 from the lower side of the first extension portion 133.

The first extension portion 133 elastically deforms while in contact with the guide surface 513, and at this time, the position of the locking flange 132 may change. As illustrated in FIG. 15, when the locking flange 132 rises, the engagement between the locking flange 132 and the locking protrusion 122 may be released, allowing the working member 120 to move forward. In other words, as the position of the locking flange 132 changes, the forward movement path of the locking protrusion 122 is released, allowing the working member 120 to move forward.

In addition, the first extension portion 133 may come into contact with the guide surface 513 of the cartridge 500, and push the cartridge 500 toward the distal end 102 of the end tool 100 by the reaction force of the force with which the cartridge 500 pushes up the first extension portion 133. When the first extension portion 133 pushes the cartridge 500 toward the distal end 102 of the end tool 100, coupling protrusions 514 arranged adjacent to the distal end 102 of the end tool 100 may be inserted into first grooves (not shown) of the first jaw 111, such that the cartridge 500 is stably mounted on the first jaw 111.

The first elastic member 130 may further include a second extension portion 134 extending from the other side of the seating portion 131. The second extension portion 134 may be curved and extend from the other side of the seating portion 131, and an end 134*a* of the second extension portion 134 may come into contact with the second jaw 112.

The first elastic member 130 may provide a restoring force in a direction in which the first jaw 111 and the second jaw 112 move away from each other in a state in which the end 134*a* of the second extension portion 134 is in contact with the second jaw 112. The first elastic member 130 may prevent the second jaw 112 from moving toward the first jaw 111 due to gravity, and this allows the first jaw 111 and the second jaw 112 to normally remain open such that body tissue may be easily interposed in the end tool 100.

The first elastic member 130 may include a pair of first extension portions 133 and a pair of second extension portions 134. The pair of first extension portions 133 and the pair of second extension portions 134 may be respectively arranged on opposite sides of the main body 121 of the working member 120, to be elastically deformed while stably engaging with the working member 120.

Figure 16:
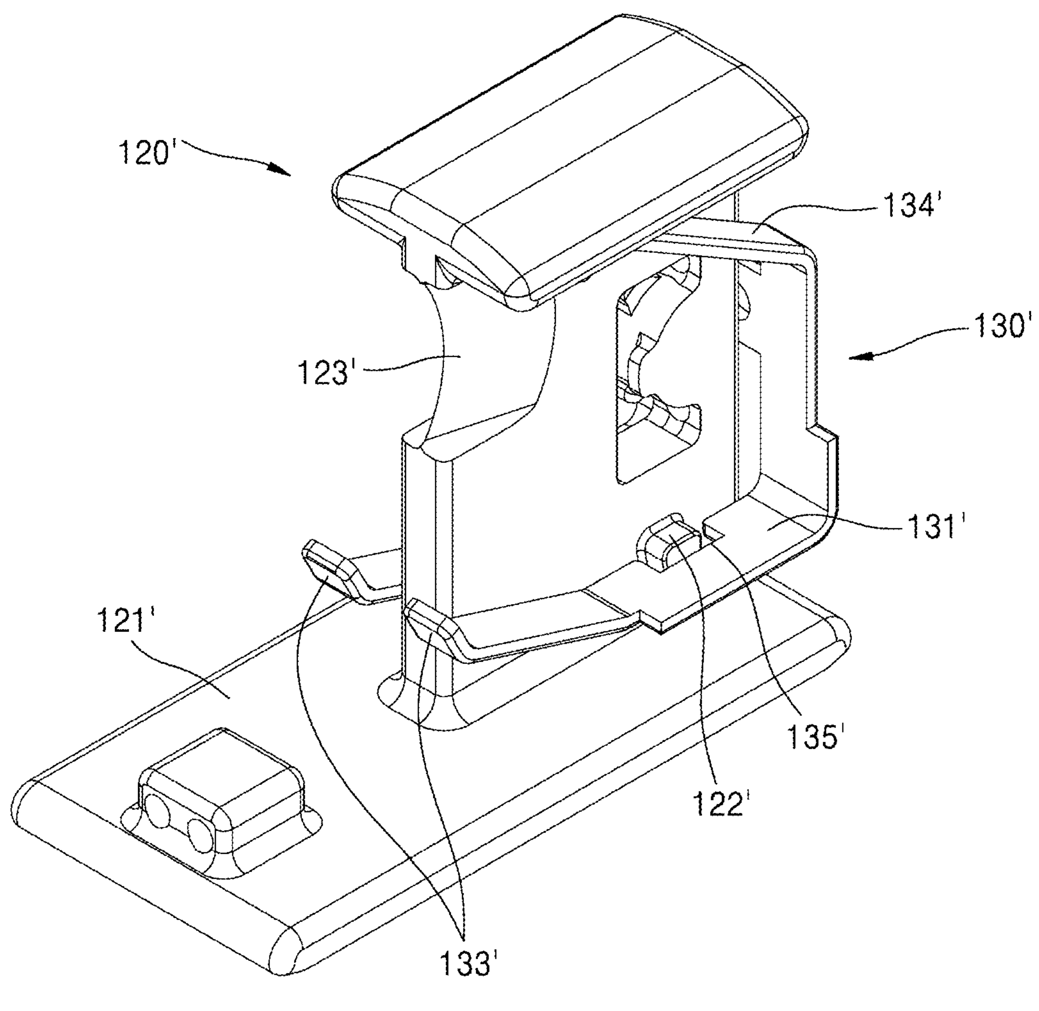
FIG. 16 is a diagram illustrating a working member and a first elastic member according to another embodiment of the present disclosure.

FIG. 16 is a diagram illustrating a working member 120' and a first elastic member 130' according to another embodiment of the present disclosure. The working member 120' and the first elastic member 130' of FIG. 16 are different from those in the embodiment of FIGS. 12 and 13 in that their partial shapes for restricting the movement of the working member 120' are modified. Hereinafter, the modified shapes will be mainly described, and a main body 121' and a blade 123' of the working member 120', or a seating portion 131', the first extension portion 133', and a second extension portion 134' of the first elastic member 130' are the same as those in the embodiment described above with reference to FIGS. 12 and 13.

Referring to FIG. 16, the working member 120' may include a locking protrusion 122', and the first elastic member 130' may include a locking groove 135' formed to correspond to the locking protrusion 122'. The first elastic member 130' may restrict the movement of the working member 120' as the locking groove 135' engages with the locking protrusion 122'. In addition, when the first elastic member 130' is elastically deformed, the position of the locking groove 135' may change, and thus, the restriction on the movement of the working member 120' due to the engagement between the working member 120' and the locking protrusion 122' may be released.

As described above, the locking protrusion 122' of the working member 120' may be formed to protrude from one side of the working member 120'. In addition, a pair of locking protrusions 122' may be provided to protrude from opposite sides of the main body 121' of the working member 120'. As such, the number, positions, and shapes of locking protrusions 122' may be variously set, and the number, positions, and shapes of locking grooves 135' may be set accordingly.

As described above, the end tool 100 of the surgical instrument 10 of the present disclosure may include the first elastic member 130, to restrict the movement of the working member 120 when the cartridge 500 is not mounted on the first jaw 111. The first elastic member 130 may be elastically deformed as the first extension portion 133 comes into contact with the cartridge 500, so as to release the restriction on the movement of the working member 120 when the cartridge 500 is mounted on the first jaw 111.

In addition, a portion of the first elastic member 130 comes into contact with the cartridge 500 to push the cartridge 500 toward the distal end 102 of the end tool 100, such that the cartridge 500 is more stably mounted on the first jaw 111. In addition, one end of the first elastic member 130 may be fixed to the second jaw 112, to allow the first jaw 111 and the second jaw 112 to normally remain open.

Second Mechanism of Lockout System

Figure 17:
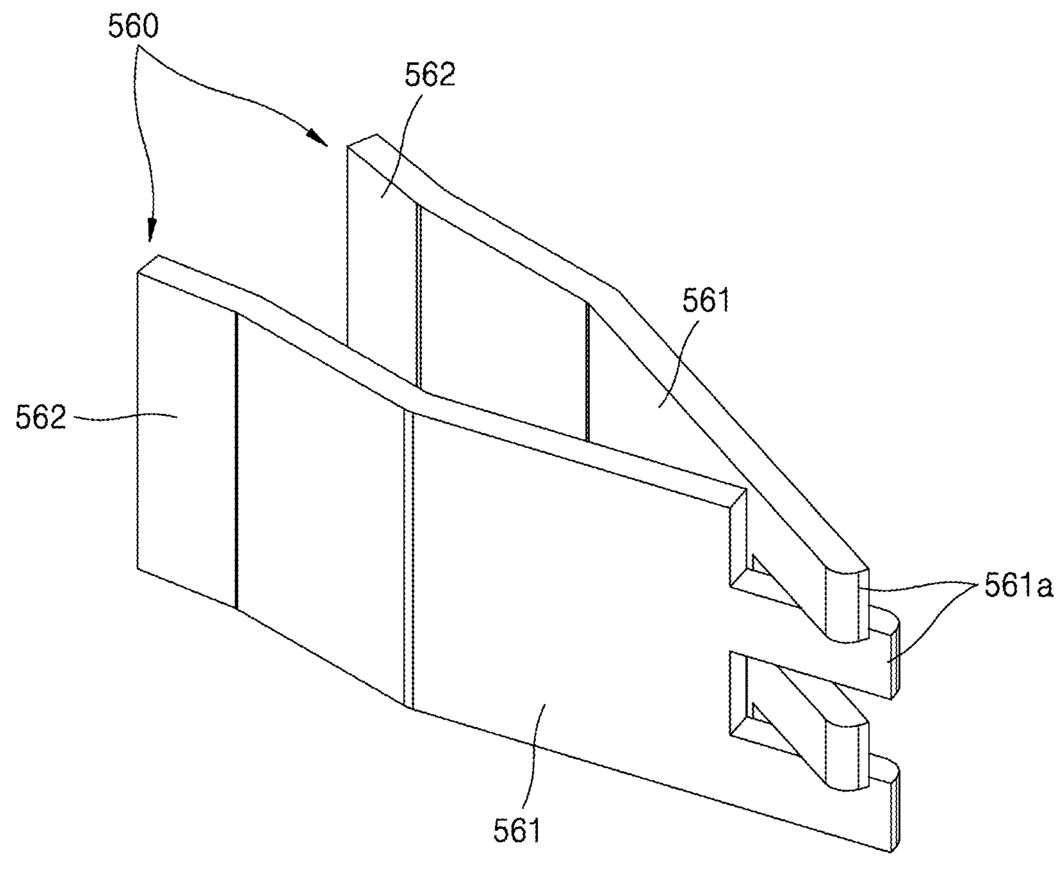
FIG. 17 is an enlarged perspective view illustrating second elastic members of the cartridge of FIG. 2.
Figure 18:
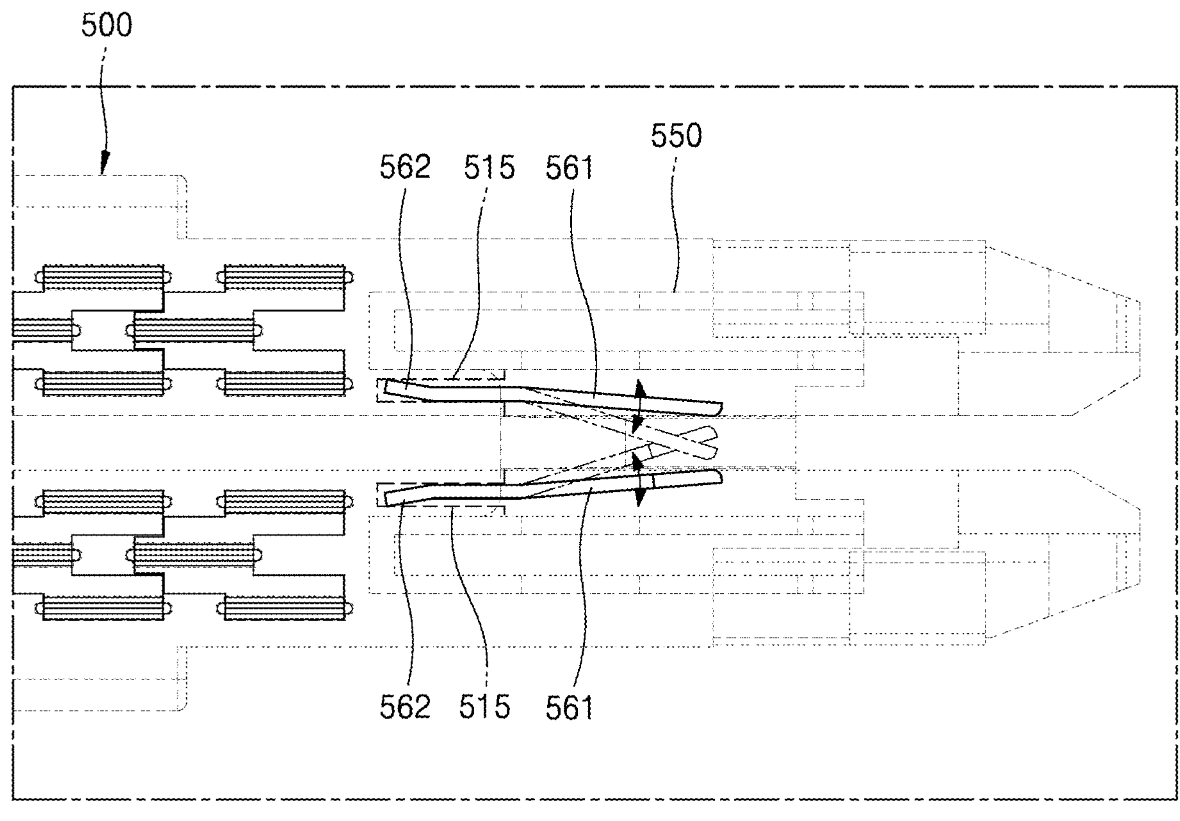
FIG. 18 is a cross-sectional view illustrating a state in which the second elastic members of FIG. 17 are arranged in a cartridge.
Figure 19:
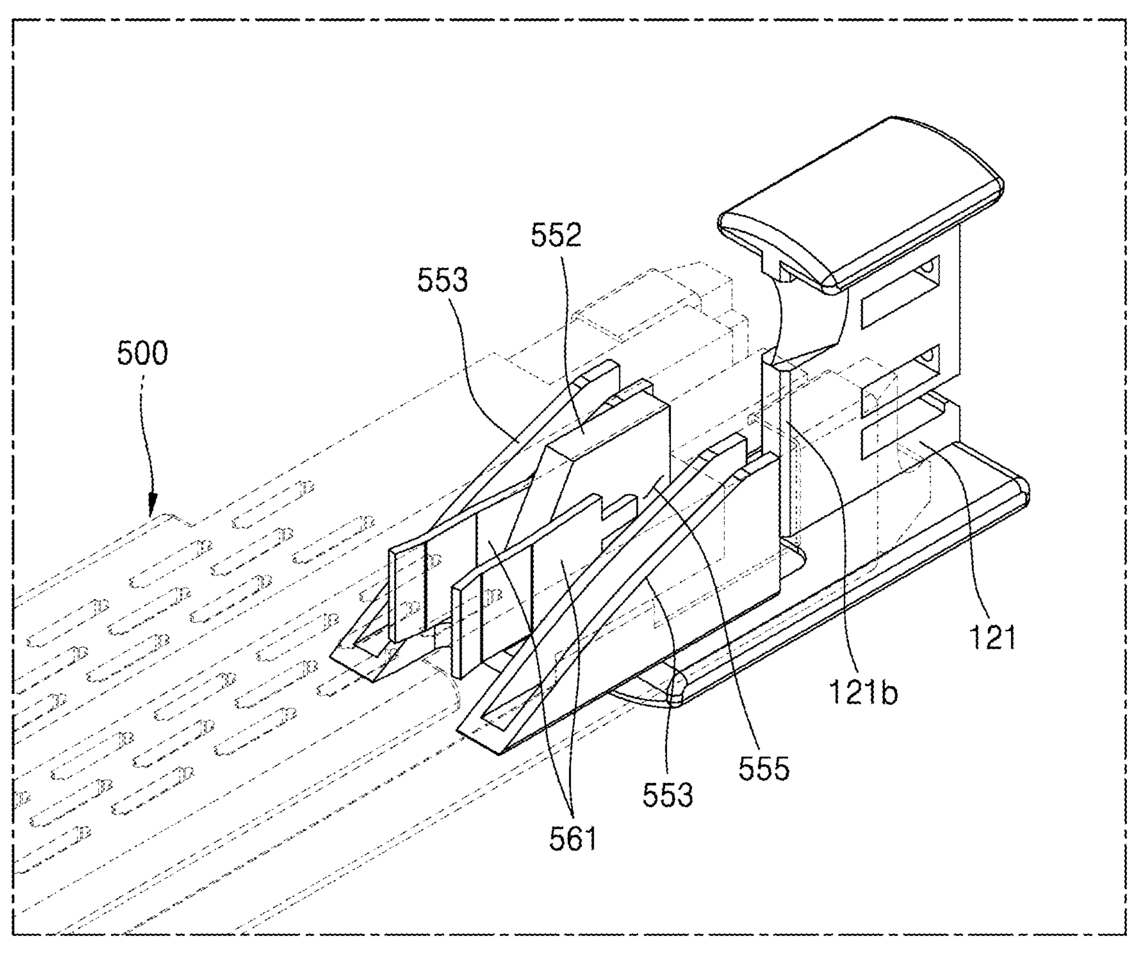
FIG. 19 is a perspective view illustrating a state in which the second elastic members of FIG. 17 are elastically deformed.
Figure 20:
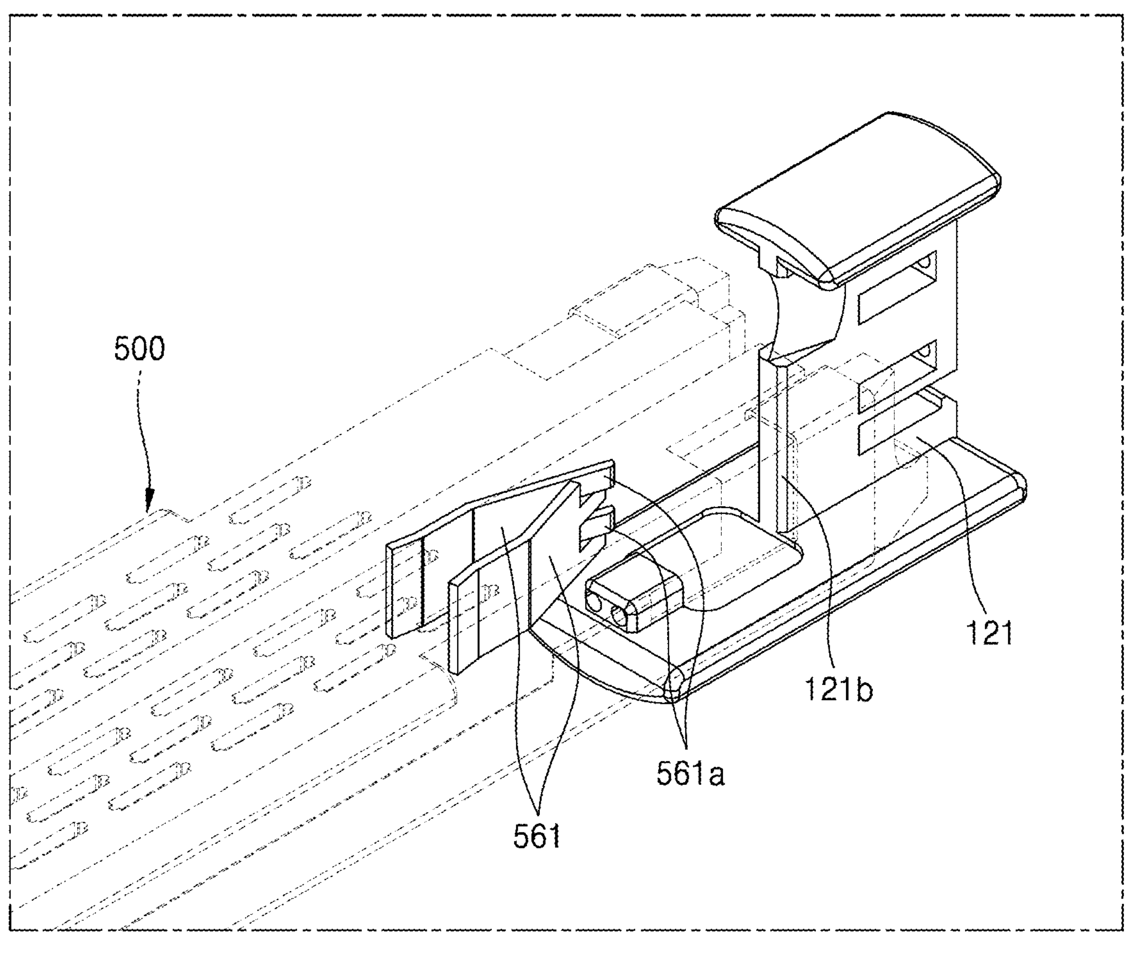
FIG. 20 is a perspective view illustrating a state in which the second elastic members of FIG. 17 are elastically restored.

FIG. 17 is an enlarged perspective view illustrating second elastic members 560 of the cartridge 500 of FIG. 2. FIG. 18 is a cross-sectional view illustrating a state in which the second elastic members 560 of FIG. 17 are arranged in the cartridge 500, FIG. 19 is a perspective view illustrating a state in which the second elastic members 560 of FIG. 17 are elastically deformed, and FIG. 20 is a perspective view illustrating a state in which the second elastic members 560 of FIG. 17 are elastically restored.

Referring to FIGS. 17 to 20, the cartridge 500 of the surgical instrument 10 according to an embodiment of the present disclosure may include the second elastic members 560. The second elastic members 560 may be arranged in the cartridge 500, to restrict the movement of the working member 120 according to the position of the wedge 550.

Hereinafter, the shape of the second elastic members 560 and an arrangement relationship between the second elastic members 560 and the wedge 550 will be described, and a second mechanism of the lockout system that prevents a forward movement of the working member 120 will be described in detail.

First, referring back to FIG. 4, the wedge 550 may include a base plate 551, a guide plate 552, and release plates 553. The wedge 550 may be arranged inside the housing 520 such that a portion of the wedge 550 comes into contact with the working member 120, and thus, the wedge 550 may move forward together with the working member 120 inside the housing 520 to eject the plurality of staples 530 out of the housing 520. That is, the wedge 550 may move from the proximal side of the housing 520 toward the distal side, and the initial position of the wedge 550 may be a point on the proximal side of the housing 520.

The base plate 551 may form a base portion of the wedge 550, and one side of the base plate 551 may be in contact with the working member 120. The guide plate 552 may be formed to protrude from the base plate 551, and the release plates 553 may be arranged on opposite sides of the guide plate 552, respectively.

The release plate 553 may be formed to have a certain inclined surface. That is, the release plate 553 may include the inclined surface 553*a* formed such that the height of the inclined surface 553*a* on the side of the proximal end 501 of the cartridge 500 is higher than the height of the first inclined surface 553*a* on the side of the distal end 502. Here, the inclined surface 553*a* of the release plate 553 may be formed as an inclined surface having one inclination, or may be formed by connecting inclined surfaces having different inclinations. Through this configuration, when the wedge 550 is moved forward by the working member 120, the release plates 553 may push up the staple 530 or the release member 540 through the inclined surfaces 553*a* so as to perform a stapling motion.

The release plates 553 may be arranged spaced apart from each other on opposite sides of the guide plate 552 to form a pair of first gaps 555. The first gaps 555 of the wedge 550 provides spaces through which the second elastic members 560 may pass when elastically deformed.

In addition, referring to FIGS. 17 to 19, the second elastic members 560 may be arranged in the cover 510, and when the wedge 550 deviates from the initial position as the wedge 550 moves forward, the second elastic members 560 may engage with the working member 120 to restrict the forward movement of the working member 120. The second elastic member 560 may include a deforming portion 561 and a fixing portion 562.

The deforming portions 561 of the second elastic members 560 are elastically deformable and are formed to cross and engage with each other. Here, ends 561*a* of the deforming portions 561 may be formed as curved surfaces.

As illustrated in FIG. 17, the deforming portions 561 of the second elastic members 560 may be cut at their end portions 561*a* to cross each other. In addition, the deforming portions 561 of the second elastic members 560 may provide restoring forces toward each other when elastically deformed to have a certain gap therebetween.

The fixing portions 562 of the second elastic members 560 are arranged spaced apart from each other by a certain distance, and may be inserted into second grooves 515 of the cover 510, respectively. That is, the second elastic members 560 may be fixed to the cover 510 by the fixing portions 562, and the deforming portions 561 formed to be curved at the fixing portions 562 may be elastically deformed to restrict the forward movement of the working member 120.

A pair of second elastic members 560 may be provided and arranged in the cover 510 as illustrated in FIGS. 17 to 20. However, the present disclosure is not limited thereto, and only one second elastic member 560 having the deforming portion 561 and the fixing portion 562 may be formed. That is, the second elastic member 560 may be provided in various shapes, types, and numbers suitable for being elastically deformed to restrict the forward movement of the working member 120.

Hereinafter, a forward movement of the working member 120 and a method of restricting the forward movement according to a process of performing a stapling motion of the surgical instrument 10 will be described.

Before the staples 530 of the cartridge 500 are ejected, the wedge 550 is arranged on the side of the proximal end 501 of the cartridge 500 and in contact with the working member 120. Here, as illustrated in FIGS. 18 and 19, the deforming portions 561 of the pair of second elastic members 560 may be elastically deformed and arranged in the first gaps 555 of the wedge 550, respectively. In other words, when the wedge 550 is arranged at the initial position, the pair of second elastic members 560 may be arranged such that the deforming portions 561 are supported by both side walls of the guide plate 552 of the wedge 550, respectively, with a certain gap therebetween.

The wedge 550 may be moved forward toward the distal end 502 of the cartridge 500 by the working member 120 to eject the plurality of staples 530. At this time, because the deforming portions 561 of the second elastic members 560 arranged in the first gaps 555 are elastically deformable, the wedge 550 and the working member 120 may pass between the pair of second elastic members 560 to move forward. When the deforming portions 561 of the pair of second elastic members 560 are no longer supported by both side walls of the guide plate 552 as the wedge 550 moves forward and deviates from the initial position, the deforming portions 561 of the pair of second elastic members 560 may provide restoring forces toward each other such that the ends 561*a* cross each other again.

After the wedge 550 performs the stapling motion while moving forward, the working member 120 moves backward toward the proximal end 101 of the end tool 100, and at this time, the wedge 550 remains at the distal end 502 of the cartridge 500. When the working member 120 moves backward, the deforming portions 561 of the pair of second elastic members 560 may be elastically deformed to provide a backward movement path for the working member 120, and when the working member 120 has passed between the second elastic members 560, the deforming portions 561 may provide restoring forces toward each other such that the ends 561*a* cross each other again.

As such, when the staples 530 no longer exists inside the housing 520, only the working member 120 returns toward the proximal end 101 of the end tool 100, and the wedge 550 does not return toward the proximal end 501 of the cartridge 500, as illustrated in FIG. 20. That is, after the plurality of staples 530 are ejected, the deforming portions 561 of the second elastic members 560 are no longer supported by both side walls of the guide plate 552 of the wedge 550 as the wedge 550 deviates from the initial position, and the ends 561*a* may be arranged to cross each other.

Therefore, when attempting to move the working member 120 forward again after the plurality of staples 530 are ejected, the deforming portion 561 of the second elastic member 560 remain crossing each other, thereby restricting the forward movement of the working member 120. In particular, the ends 561*a* of the deforming portions 561 may be formed as curved surfaces, and contact portions 121*b* of the main body 121, which may come into contact with the respective ends 561*a* of the deforming portions 561 when the working member 120 moves forward, may also be formed to have certain curvatures. Through this configuration, even when the working member 120 moves forward to come into contact with the deforming portions 561 of the second elastic members 560 after the plurality of staples 530 are ejected, it is possible to prevent the working member 120 from passing between the pair of second elastic members 560.

As described above, in the surgical instrument according to an embodiment of the present disclosure, the end tool may include the first elastic member such that, when the cartridge is not arranged in the first jaw, the first elastic member may restrict a forward movement of the working member. In addition, in the surgical instrument according to an embodiment of the present disclosure, the cartridge may include the second elastic member such that even when the cartridge is arranged in the first jaw, the second elastic member may restrict the forward movement of the working member after the staples are ejected.

Through this configuration, the present disclosure implements a lockout system that prevents the working member from moving forward to cut body tissue when staples are not arranged in the surgical instrument, thereby providing a surgical instrument with improved safety and usability.

The present disclosure has been described with reference to the preferred embodiments. It will be understood by those of skill in the art that the present disclosure may be implemented in a modified form without departing from the intrinsic characteristics of the present disclosure. Therefore, the disclosed embodiments are to be considered in a descriptive sense only, and not for purposes of limitation. The scope of the present disclosure is in the claims rather than the above descriptions, and all differences within the equivalent scope should be construed as being included in the present disclosure.

A surgical instrument according to the present disclosure includes a structure that prevents a working member from moving forward to cut body tissue when a cartridge is not arranged or when a cartridge without staples is arranged, thus failing to suture a cut site due to the absence of staples, thereby improving the safety and usability of the surgical instrument.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A surgical instrument comprising an end tool rotatable in at least one direction, the end tool comprising:

- a jaw unit having a first jaw configured to accommodate a cartridge, and a second jaw facing the first jaw;
- a working member configured to be movable in a lengthwise direction of the first jaw; and
- a first elastic member disposed on a proximal side of the first jaw and configured to restrict a movement of the working member depending on whether the cartridge is accommodated in the first jaw,
- wherein when the cartridge is disposed in the first jaw, one end of the first elastic member is supported by the cartridge and then elastically deformed, and the first elastic member releases a restriction on the movement of the working member.

2. The surgical instrument of claim 1, wherein the working member includes a locking protrusion protruding from one side of a main body and configured to restrict the movement of the working member when the cartridge is not disposed in the first jaw.

3. The surgical instrument of claim 2,

- wherein the working member has a first slit defined by cutting a portion of the main body, and
- wherein the locking protrusion protrudes from the main body toward the first slit.

4. The surgical instrument of claim 3, wherein the first elastic member comprises a locking flange disposed in the first slit and configured to restrict the movement of the working member by engaging with the locking protrusion when the cartridge is not disposed in the first jaw.

5. The surgical instrument of claim 4, wherein, when the cartridge is disposed in the first jaw, a position of the locking flange changes due to elastic deformation of the first elastic member, and the restriction on the movement of the working member caused by an engagement between the locking flange and the locking protrusion is released, and the working member becomes movable forward toward a distal side of the first jaw.

6. The surgical instrument of claim 2, wherein the first elastic member includes a locking groove corresponding to the locking protrusion, and configured to restrict the movement of the working member by engaging with the locking protrusion when the cartridge is not disposed in the first jaw.

7. The surgical instrument of claim 6, wherein the locking groove is concavely defined at one side of a seating portion of the first elastic member, the seating portion being seated on the first jaw.

8. The surgical instrument of claim 6, wherein, when the cartridge is disposed in the first jaw, a position of the locking groove changes due to elastic deformation of the first elastic member, and the restriction on the movement of the working member caused by an engagement between a locking flange and the locking protrusion is released, and the working member becomes movable forward toward a distal side of the first jaw.

9. The surgical instrument of claim 1, wherein the first elastic member includes a first extension portion configured to contact a guide surface disposed to be inclined on one side of the cartridge, and become elastically deformed.

10. The surgical instrument of claim 9, wherein the first elastic member further comprises:

- a seating portion configured to be seated on the first jaw; and
- a second extension portion extending in a curved shape from the seating portion, and having a portion configured to contact the second jaw.

11. The surgical instrument of claim 10, wherein the first extension portion is defined to be inclined and a portion of the first extension portion forms a predetermined angle with the seating portion.

12. The surgical instrument of claim 10, wherein the second extension portion is disposed between the second jaw and the working member and is configured to restrict rotation of the second jaw.

* * * * *